United States Patent [19]

Ōtake et al.

[11] Patent Number: 4,710,564
[45] Date of Patent: Dec. 1, 1987

[54] ANTHRACYCLINE COMPOUNDS

[75] Inventors: Noboru Ōtake, Yokohama; Kuniaki Tatsuta; Shigeyuki Mizobuchi, both of Tokyo; Nobuyasu Komeshima, Maebashi; Shohachi Nakajima, Maebashi; Hiroyuki Kawai, Maebashi; Atsuo Odagawa, Maebashi, all of Japan

[73] Assignee: Microbial Chemistry Research Foundation, Tokyo, Japan

[21] Appl. No.: 818,867

[22] Filed: Jan. 14, 1986

[30] Foreign Application Priority Data

Jan. 18, 1985 [JP] Japan ................................. 60-7196
Mar. 1, 1985 [JP] Japan ................................. 60-40866

[51] Int. Cl.[4] ........................................... C07H 15/24
[52] U.S. Cl. ................................................... 536/6.4
[58] Field of Search ........................... 536/64; 514/34

[56] References Cited

U.S. PATENT DOCUMENTS 4,301,277 11/1981 Acton et al. ......................... 536/6.4
4,374,980 2/1983 Umezawa .
4,464,529 8/1984 Mosher et al. ...................... 536/6.4

FOREIGN PATENT DOCUMENTS 3012665 11/1980 Bangladesh .
2048245 12/1980 United Kingdom .
2124224 2/1984 United Kingdom .

Primary Examiner—J. R. Brown
Assistant Examiner—Elli Peselel
Attorney, Agent, or Firm—Ladas & Parry

[57] ABSTRACT

Disclosed is a novel anthracycline compound of the following formula (I):

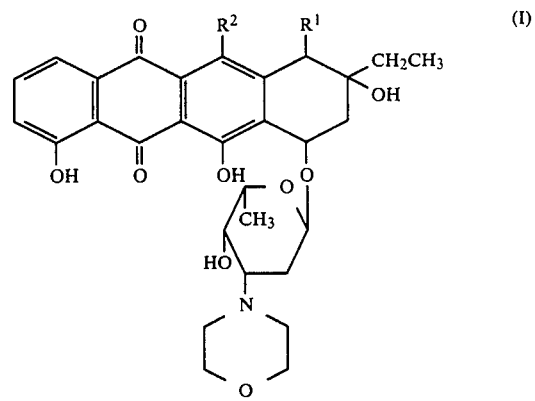

wherein $R^1$ and $R^2$ are each a hydroxyl group or a hydrogen atom and satisfy the condition that, when $R^2$ is a hydroxyl group, $R^1$ is a hydroxyl group or a hydrogen atom, whereas, when $R^2$ is a hydrogen atom, $R^1$ is a hydrogen atom, or an acid addition salt thereof.

These compounds can be contained as active ingredients in antitumor agents, whereby good results are attainable.

3 Claims, 19 Drawing Figures

EFFECT OF 3'-DEAMINO-3'-(4-MORPHOLINYL) DERIVATIVES OF THE PRESENT INVENTION ON THE HEART

○ ADRIAMYCIN
● 3'-DEAMINO-3'-(4-MORPHOLINYL) R20Y5
△ 3'-DEAMINO-3'-(4-MORPHOLINYL) R20X2
□ 3'-DEAMINO-3'-(4-MORPHOLINYL) R20X n=3~4
n=5~6
n=4~6
n=3

STUDENT TEST:
* P < 0.05
† P < 0.01 n: NUMBER OF GOLDEN HAMSTERS

FIG. 2 INFRARED ABSORPTION SPECTRUM

FIG. 5 INFRARED ABSORPTION SPECTRUM

INFRARED ABSORPTION SPECTRUM

FIG. 11 INFRARED ABSORPTION SPECTRUM

WAVE NUMBER (cm$^{-1}$)
INFRARED ABSORPTION SPECTRUM

FIG. 17 INFRARED ABSORPTION SPECTRUM

ANTHRACYCLINE COMPOUNDS

BACKGROUND OF THE INVENTION

1. Technical Field

This invention relates to novel anthracycline compounds and uses thereof. More particularly, the invention relates to 3'-deamino-3'-(4-morpholinyl) derivatives of 13-deoxocarminomycin (hereinafter referred to as "R20X") and 10-hydroxy-13-deoxocarminomycin (hereinafter referred to as "R20X2", R20X and R20X2 being referred to collectively as "R20 substances") which are anthracycline compounds having antitumor activity and to a 3'-deamino-3'-(4-morpholinyl) derivative of 11-deoxy-13-deoxocarminomycin (hereinafter referred to as "R20Y5") which is also an anthracycline compound having antitumor activity.

2. Prior Art

Anthracycline compounds heretofore known are, for example, daunomycin (U.S. Pat. No. 3,616,242) and adriamycin (U.S. Pat. No. 3,590,028) obtained from the culture broths of actinomycetes, and these compounds are widely used for clinical purposes as antitumor agents. They, however, are not satisfactorily acceptable pharmaceutical agents since they cause strong side effects while exhibiting remarkable antitumor activity.

As a compound relevant to the 3'-deamino-3'-(4-morpholinyl) derivatives of the present invention, Rivola, G. et al. obtained R20X which is a leading compound of the derivatives from the culture broth of *Streptomyces peucetius* var. *carminatus* (DSM 1524, ATCC 31502, FRI 4929, Farmitalia Carlo Erba collection of microorganisms No. DR 81 F.I.) and have reported that the compound has antitumor activity (West German Patent Application Laid-Open Pub. No. 3,012,665). Giuseppe Cassinelli et al. also obtained R20Y5 which is another leading compound of the above derivatives from the culture broth of a mutant strain of *Streptomyces peucetius* var. *caecius*, i.e., *Streptomyces peucetius* var. *aureus* and have reported that this compound has antitumor activity (Japanese Patent Application Laid-Open Pub. No. 76896/1980).

Further, various derivatives of adriamycin, daunomycin and carminomycin were synthesized as morpholinyl derivatives of anthracycline compounds and have been reported to have antitumor activity (Japanese Patent Application Laid-Open Pub. No. 163393/1982; U.S. Pat. No. 4,301,277; Japanese Patent Application Laid-Open Pub. No. 212484/1984; Japanese Patent Application Laid-Open Pub. No. 212499/1984; Mosher, C. W. et al., J. Med. Chem. 25 pp. 18–24 (1982); Johnston, J. B., Biochemical Pharmacology 32(21) pp. 3255–3258 (1983); Acton, E. M., J. Med. Chem. 27 pp. 638–645 (1984)).

As far as we are aware, however, these compounds are not again necessarily acceptable on the point of high antitumor activity or low toxicity.

Anthracycline compounds form a group of useful antitumor agents, so that there has been constant demand for better anthracycline compounds.

SUMMARY OF THE INVENTION

The present invention contributes toward meeting the above-mentioned demand.

More particularly, the present invention provides a novel anthracycline compound represented by the formula (I) shown hereinbelow and also an acid addition salt thereof.

The antitumor agent according to this invention comprises as an active ingredient a safe and effective amount of a novel anthracycline compound of the following formula (I):

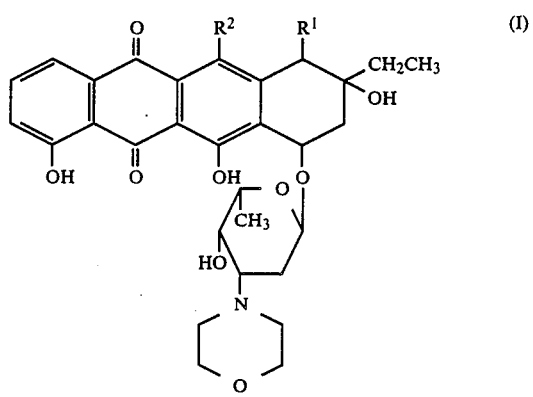

wherein $R^1$ and $R^2$ are each a hydroxyl group or a hydrogen atom and satisfy the condition that, when $R^2$ is a hydroxyl group, $R^1$ is a hydroxyl group or a hydrogen atom, whereas, when $R^2$ is a hydrogen atom, $R^1$ is a hydrogen atom, or an acid addition salt thereof and a pharmaceutically acceptable carrier.

This invention further provides a method of treating tumors in animals which comprises administering to an animal in need of such treatment a safe and effective amount of the novel anthracycline compound of the formula (I) or an acid addition salt thereof.

DETAILED DESCRIPTION OF THE INVENTION

Compounds of the present invention

I. Chemical structure

The novel anthracycline compounds of this invention have a chemical structure as shown by the following formula (II) in the case where $R^2$ in the above formula (I) is a hydroxyl group, and have a chemical structure as shown by the formula (III) in the case where $R^2$ is a hydrogen atom.

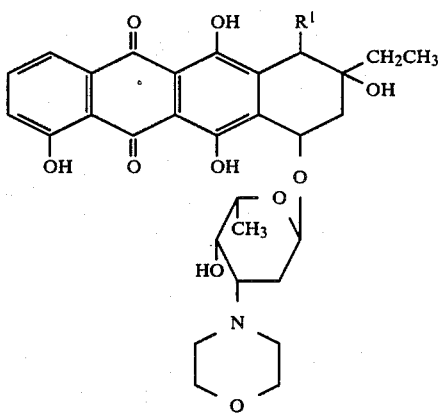

wherein $R^1$ is a hydroxyl group or a hydrogen atom.

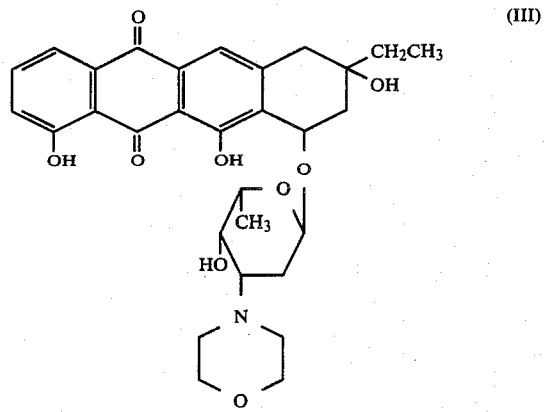

II. Physicochemical properties

A. 3'-Deamino-3'-(4-morpholinyl) R20X of the formula (II) wherein $R^1$ is a hydrogen atom
(1) Appearance: Reddish brown powder
(2) Elementary analysis:

|  | C | H | N | O |
|---|---|---|---|---|
| Found (%) | 62.98 | 6.31 | 2.40 | 28.31 |
| Calcd. (%) | 63.26 | 6.19 | 2.46 | 28.09 |

Figure 1:
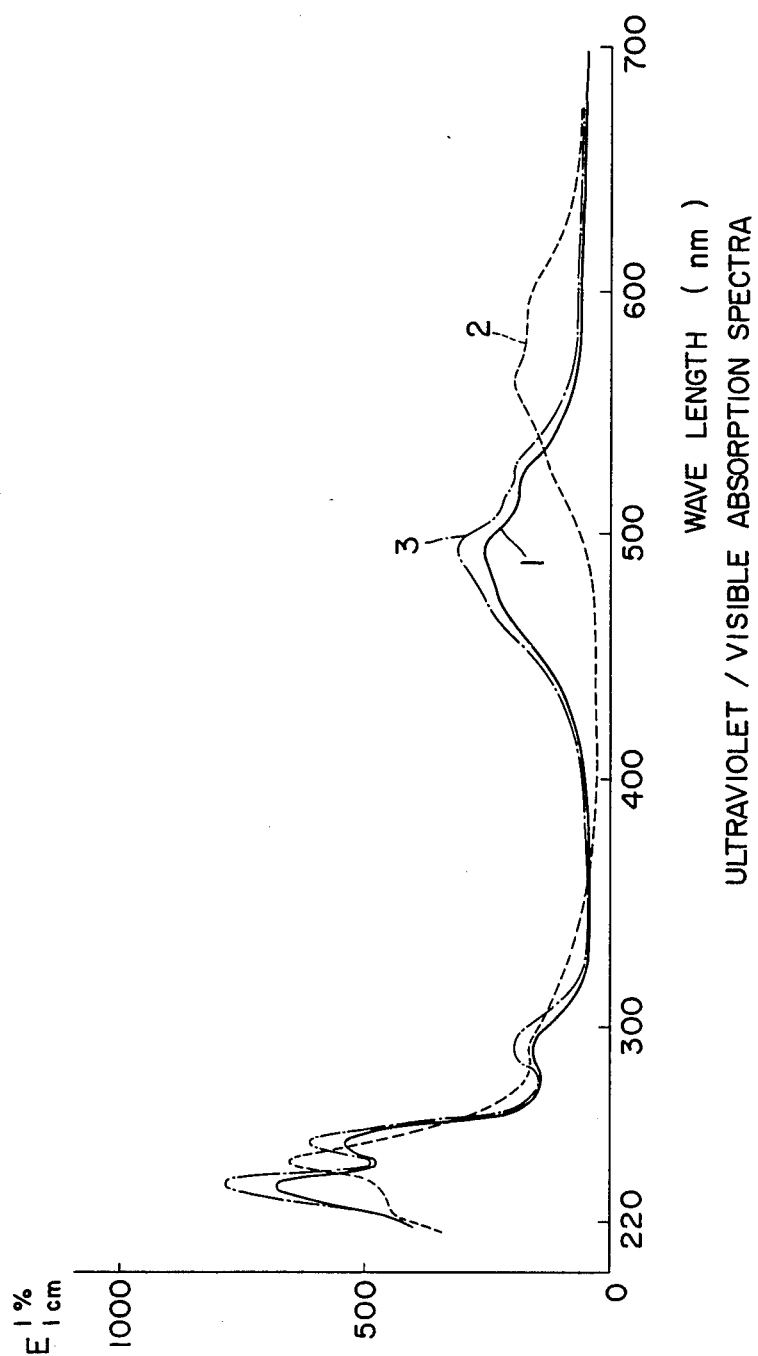
FIG. 1 is a graph showing the ultraviolet/visible absorption spectra of 3'-deamino-3'-(4-morpholinyl) R20X, the curve 1 showing the spectrum in methanol, the curve 2 the spectrum in methanol plus 0.1N HCl, and the curve 3 the spectrum in methanol plus 0.1N NaOH.

(3) Molecular weight: 569.6
(4) Melting point: 143°–144° C. (decomposed)
(5) Specific rotatory power: $[\alpha]_D^{25} = +76°$ (C: 0.05 in methanol)
(6) Ultraviolet and visible absorption spectrum: Shown in FIG. 1.

$\lambda_{max}$ nm ($E_1$ $_{cm}^{1\%}$)

(a) Methanol: 234(683), 252(545), 292(158), 464(205), 492(261), 508(194), 524(181), 575(18)
(b) Acidic methanol: 234(783), 252(612), 292(192), 466(233), 492(315), 510(227), 524(202)
(c) Alkaline methanol: 226(422), 243(653), 290(166), 528(126), 562(192), 596(162)

Figure 2:
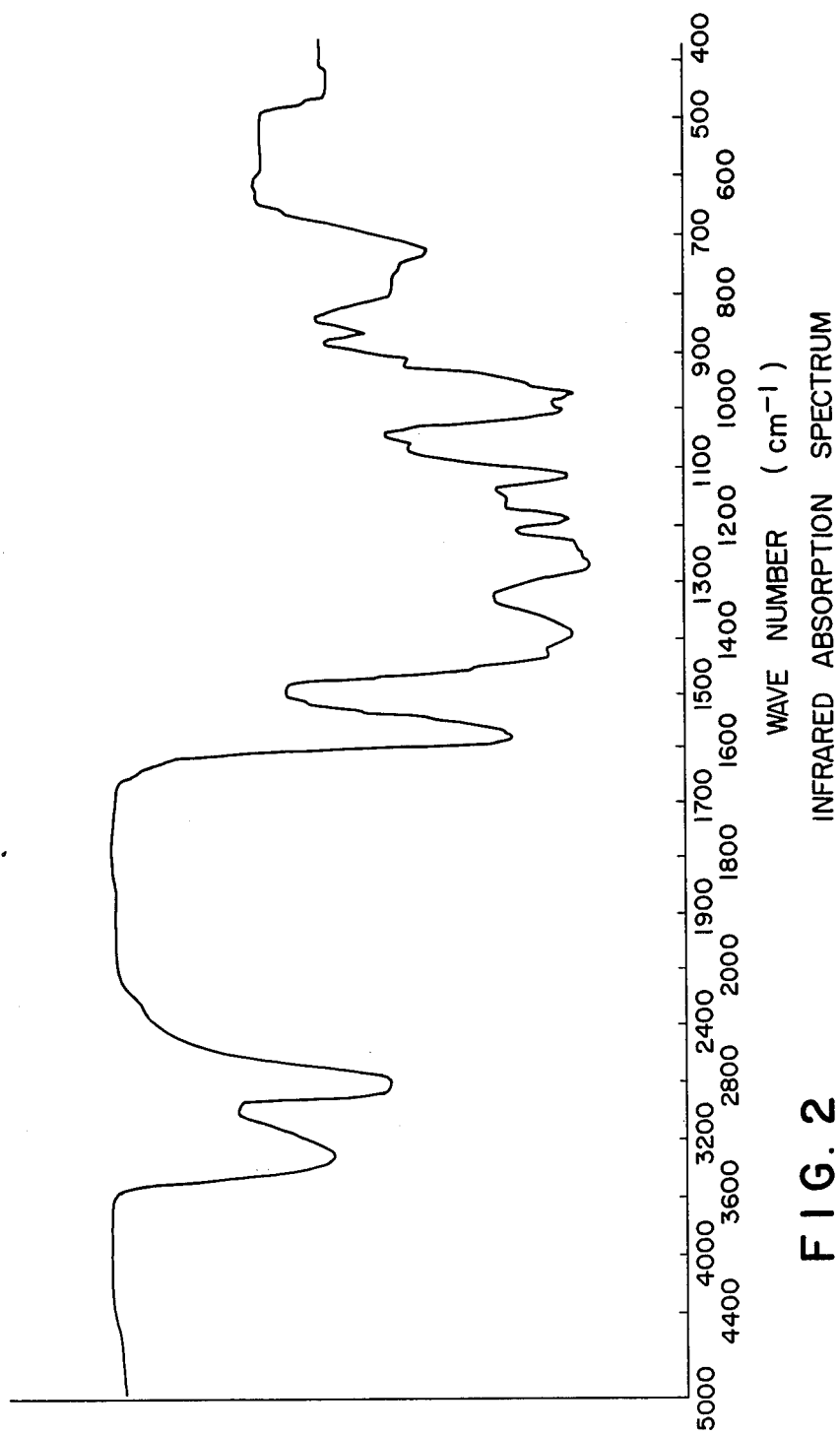
FIG. 2 is a graph showing the infrared absorption spectrum of 3'-deamino-3'-(4-morpholinyl) R20X.
Figure 3:
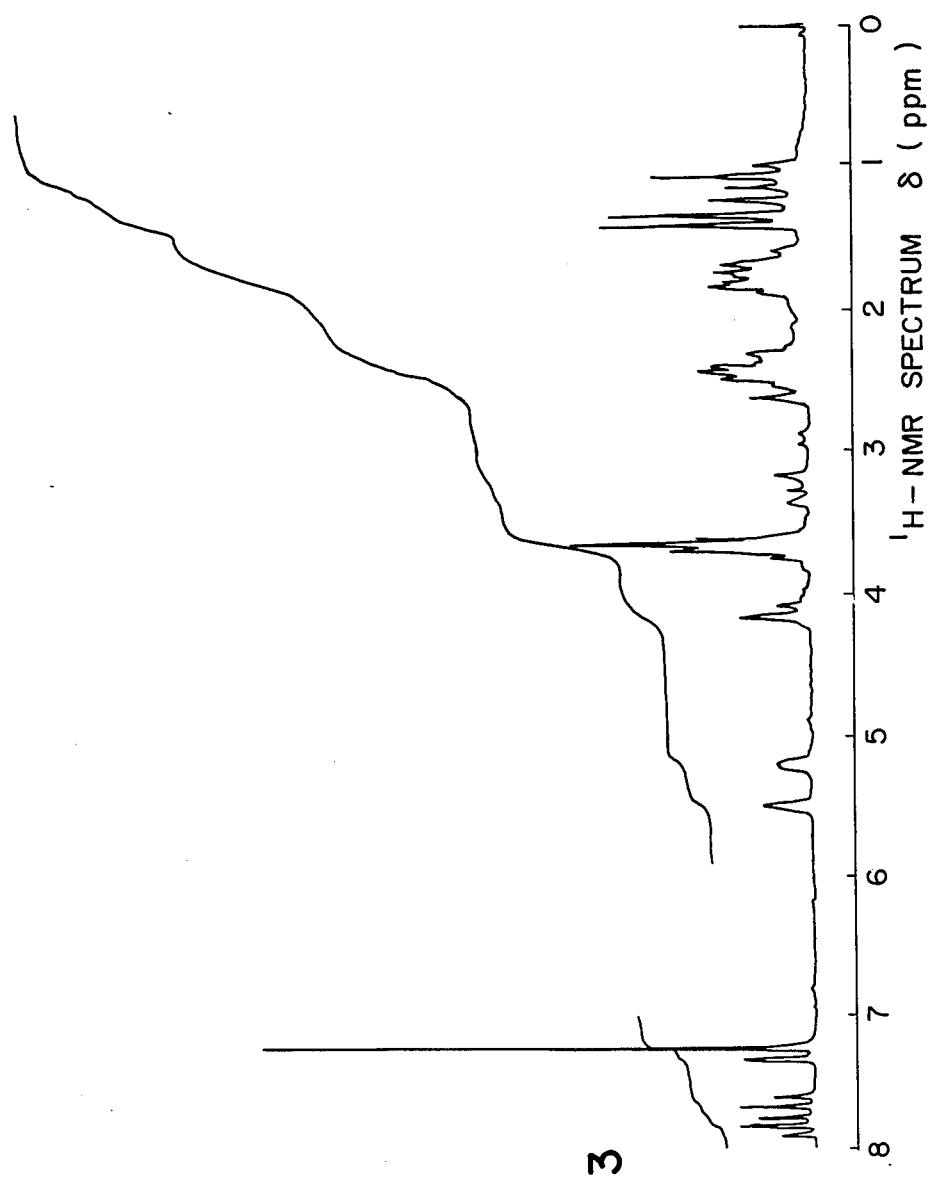
FIG. 3 is a graph showing the $^1$H-NMR spectrum of 3'-deamino-3'-(4-morpholinyl) R20X in deuterochloroform.

(7) Infrared absorption spectrum (potassium bromide tablet): Shown in FIG. 2
(8) Proton NMR spectrum (100 MHz, in deuterochloroform): Shown in FIG. 3.
(9) Rf Value (on silica gel plate 60F$_{254}$ supplied by Merck & Co., Inc.):

| Solvent system | Rf Value |
|---|---|
| Chroloform:methanol (10:1) | 0.42 |
| Chloroform:methanol:acetic acid (10:1:1) | 0.61 |
| Chloroform:methanol:triethylamine (10:1:1) | 0.72 |

(10) Solubility: Soluble in acidic water, basic water, methanol, ethanol, propanol, acetone, ethyl acetate, and chloroform but insoluble in water, hexane, cyclohexane, diethyl ether, and petroleum ether.

B. 3'-Deamino-3'-(4-morpholinyl) R20X2 of the formula (II) wherein $R^1$ is a hydroxyl group
(1) Appearance: Brown powder
(2) Elementary analysis:

|        | C     | H    | N    | O     |
|--------|-------|------|------|-------|
| Found (%) | 61.32 | 6.30 | 2.26 | 30.12 |
| Calcd. (%) | 61.53 | 6.02 | 2.39 | 30.06 |

(3) Molecular weight: 585.6

(4) Melting point: 155°–157° C. (decomposed)

(5) Specific rotatory power: $[\alpha]_D^{20} = +306°$ (C: 0.05 in $CHCl_3$)

Figure 4:
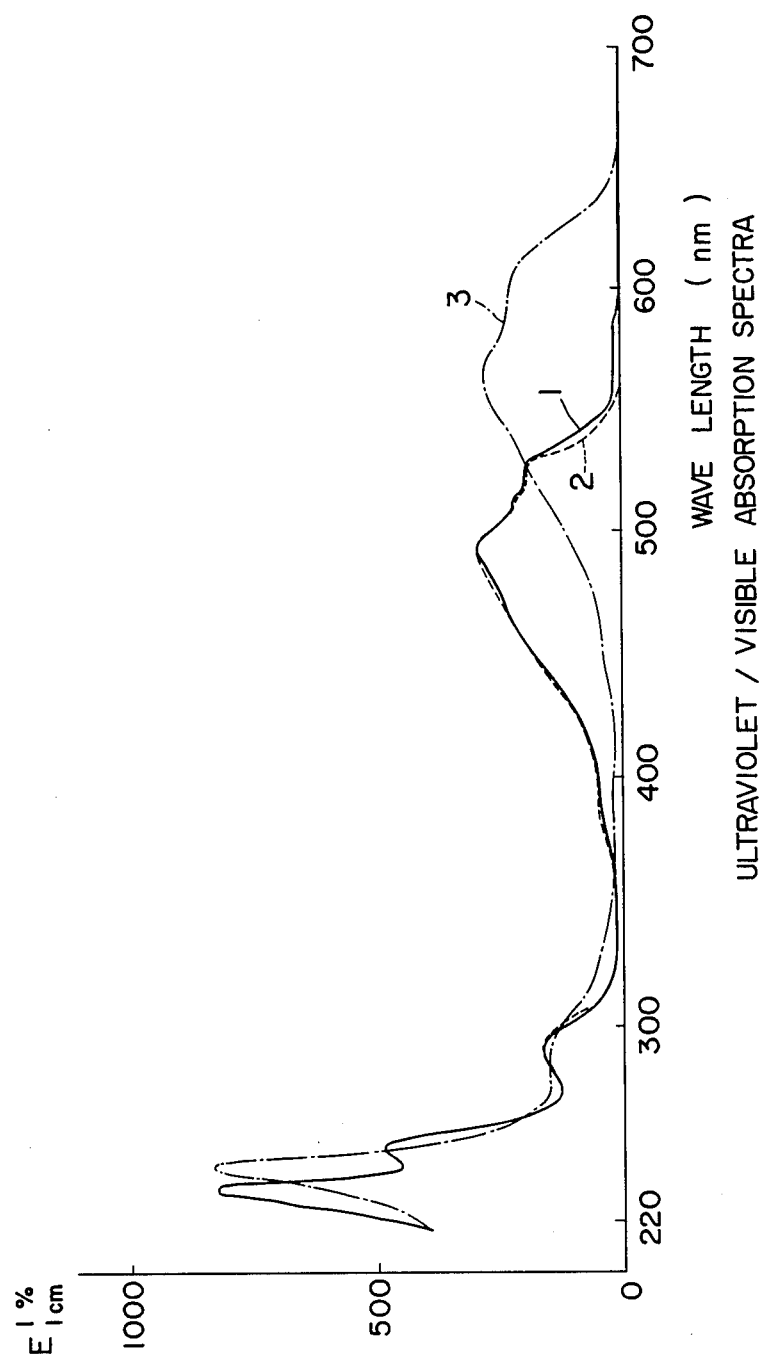
FIG. 4 is a graph indicating the ultraviolet/visible absorption spectra of 3'-deamino-3'-(4-morpholinyl) R20X2, the curve 1 indicating the spectrum in methanol, the curve 2 the spectrum in methanol plus 0.1N HCl, and the curve 3 the spectrum in methanol plus 0.1N NaOH.

(6) Ultraviolet and visible absorption spectrum: Shown in FIG. 4.

$\lambda_{max}$ nm ($E_{1\ cm}^{1\%}$)

(a) Methanol: 234(821), 252(478), 290(153), 468(241), 480(263), 492(295), 514(216), 526(196), 582(17)

(b) Acidic methanol: 234(805), 252(479), 290(155), 468(246), 480(273), 492(297), 512(214), 526(193)

(c) Alkaline methanol: 242(831), 292(149), 534(212), 564(280), 600(226)

Figure 5:
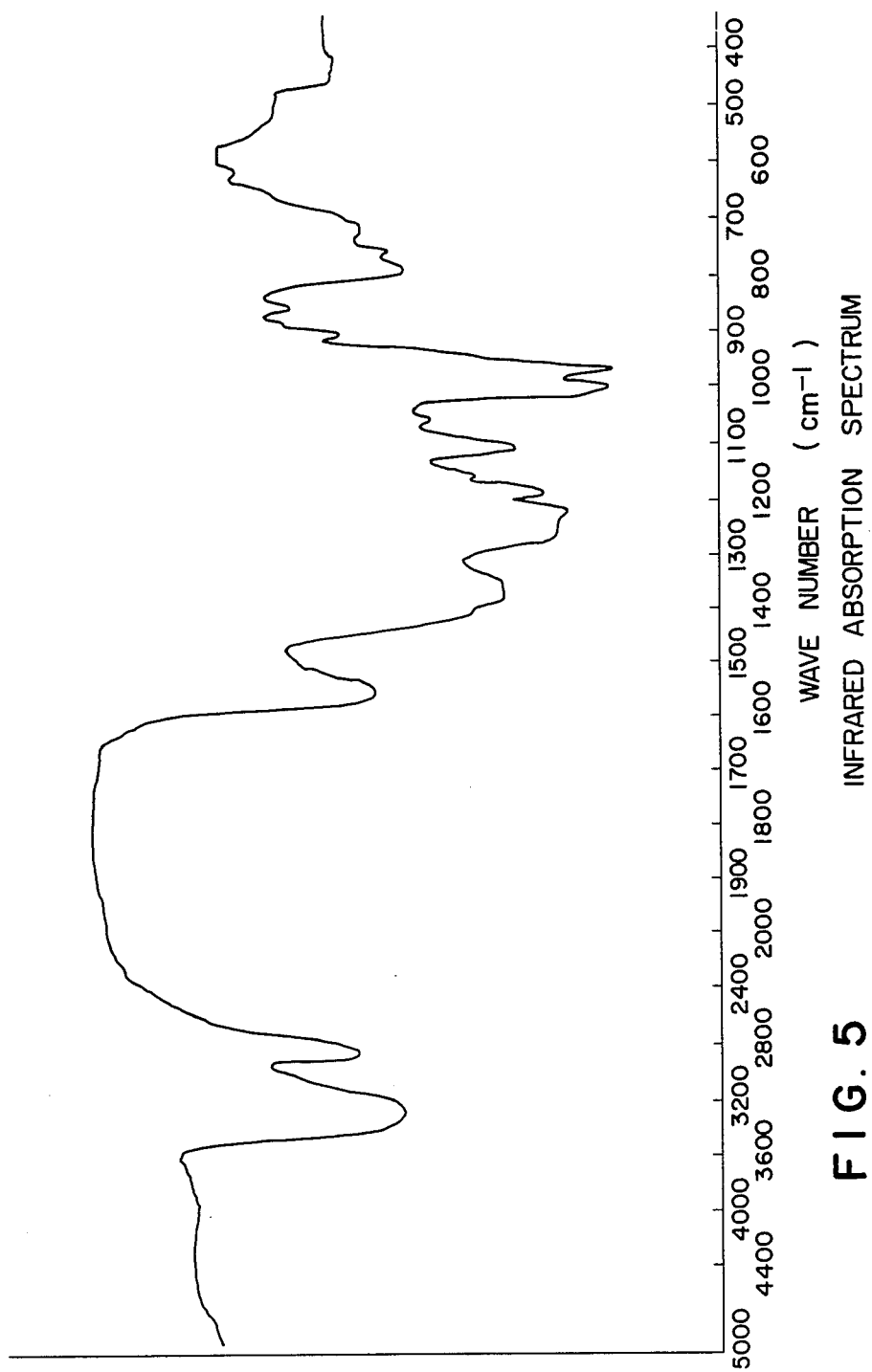
FIG. 5 is a graph indicating the infrared absorption spectrum of 3'-deamino-3'-(4-morpholinyl) R20X2.

(7) Infrared absorption spectrum (potassium bromide tablet): Shown in FIG. 5

Figure 6:
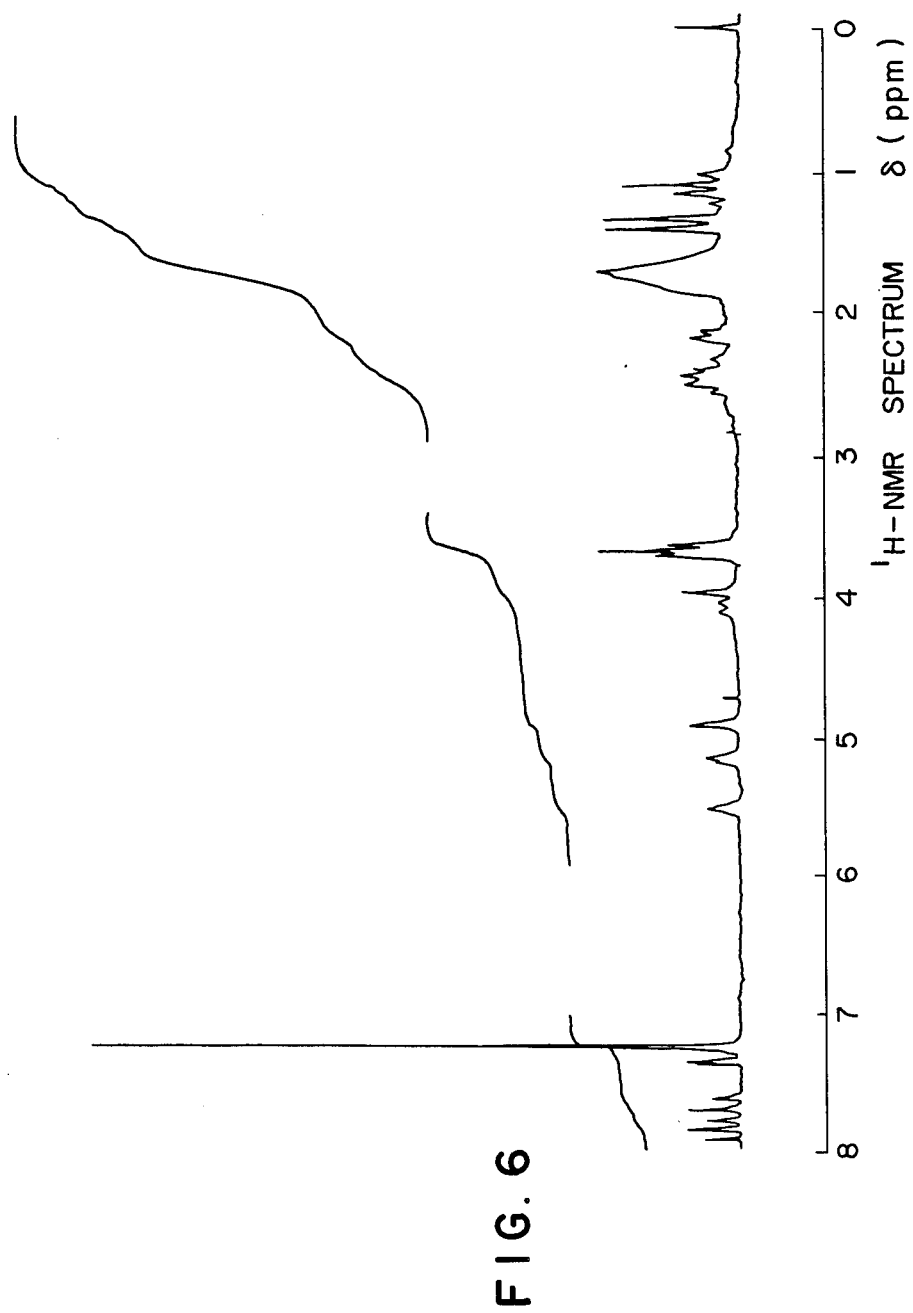
FIG. 6 is a graph indicating the $^1$H-NMR spectrum of 3'-deamino-3'-(4-morpholinyl) R20X2 in deuterochloroform.

(8) Proton NMR spectrum (100 MHz, in deuterochloroform): Shown in FIG. 6.

(9) Rf Value (on silica gel plate 60F$_{254}$ supplied by Merck & Co., Inc.):

| Solvent system | Rf Value |
|---|---|
| Chloroform:methanol (10:1) | 0.40 |
| Chloroform:methanol:acetic acid (10:1:1) | 0.59 |
| Chloroform:methanol:triethylamine (10:1:1) | 0.72 |

(10) Solubility: Soluble in acidic water, basic water, methanol, ethanol, propanol, acetone, ethyl acetate, and chloroform but insoluble in water, hexane, cyclohexane, diethyl ether, and petroleum ether.

C. 3'-Deamino-3'-(4-morpholinyl) R20Y5 of the formula (III)

(1) Appearance: Yellow powder (2) Elementary analysis:

|        | C     | H    | N    | O     |
|--------|-------|------|------|-------|
| Found (%) | 64.78 | 6.53 | 2.59 | 26.10 |
| Calcd (%) | 65.09 | 6.37 | 2.53 | 26.01 |

(3) Molecular weight: 553(FD-MS)

(4) Melting point: 132°–135° C.

(5) Specific rotatory power: $[\alpha]_D^{15} = +195.2°$ (C: 0.125 in methanol)

Figure 7:
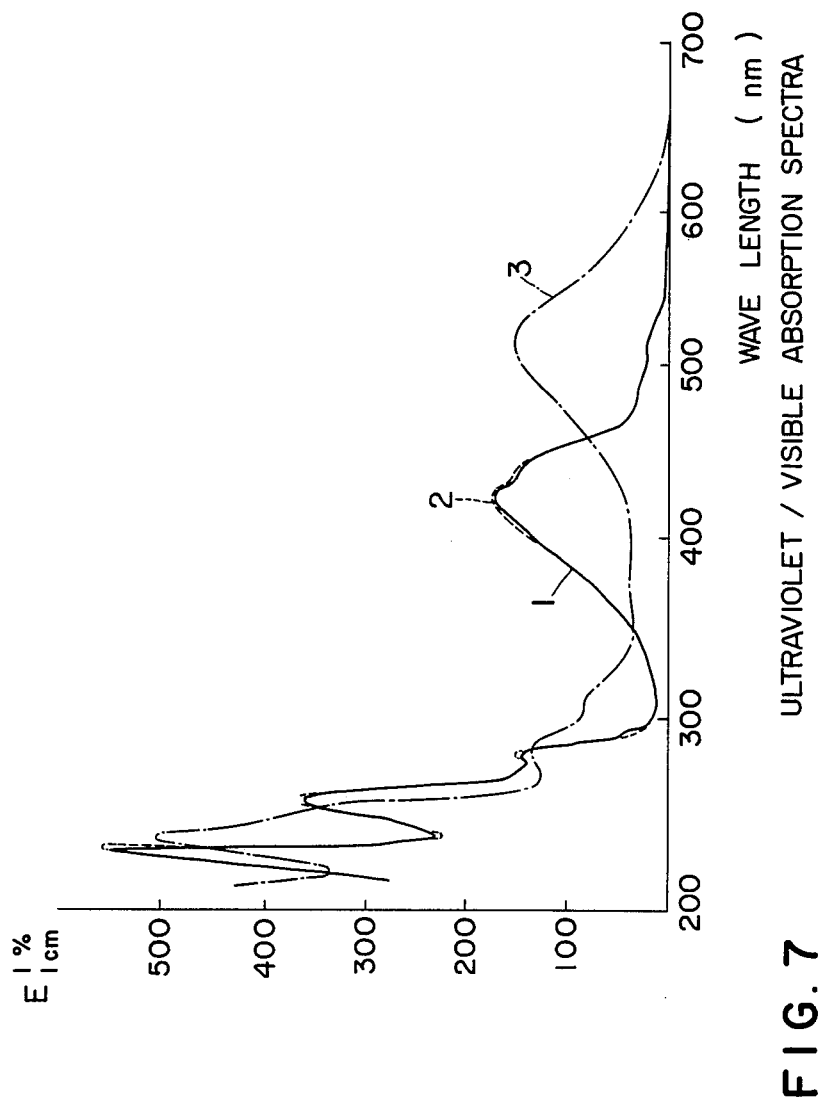
FIG. 7 is a graph showing the ultraviolet/visible absorption spectra of 3'-deamino-3'-(4-morpholinyl) R20Y5, the curve 1 showing the spectrum in methanol, the curve 2 the spectrum in methanol plus 0.1N HCl, and the curve 3 the spectrum in methanol plus 0.1N NaOH.

(6) Ultraviolet and visible absorption spectrum: Shown in FIG. 7.

$\lambda_{max}$ nm ($E_{1\ cm}^{1\%}$)

(a) Methanol: 229(541.6), 257(360.8), 289(164.8), 429(186.8)

(b) Acidic methanol: 228(552.8), 257(370.8), 291(169.2), 431(192.8)

(c) Alkaline methanol: 237(492.8), 252sh(375.6), 292(156.8), 520(163.6)

Figure 8:
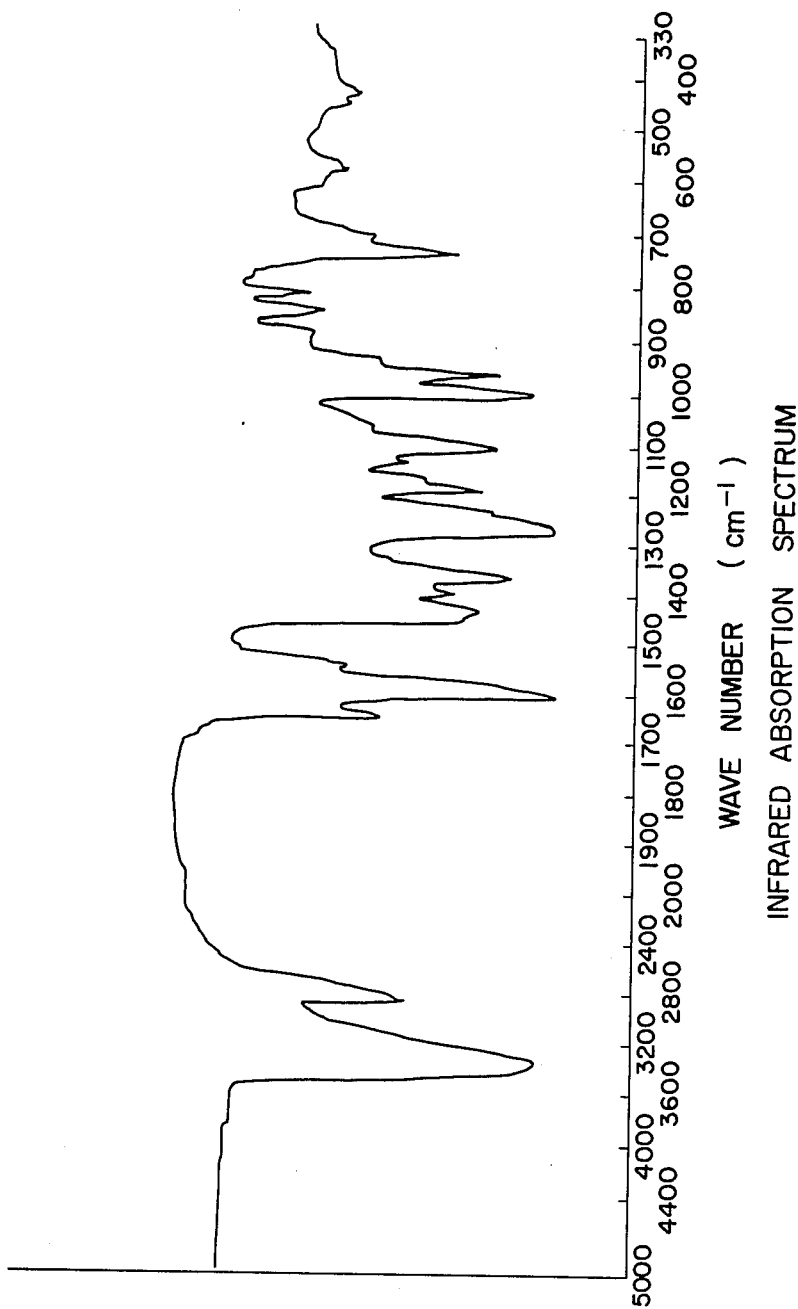
FIG. 8 is a graph showing the infrared absorption spectrum of 3'-deamino-3'-(4-morpholinyl) R20Y5.

(7) Infrared absorption spectrum (potassium bromide tablet): Shown in FIG. 8.

Figure 9:
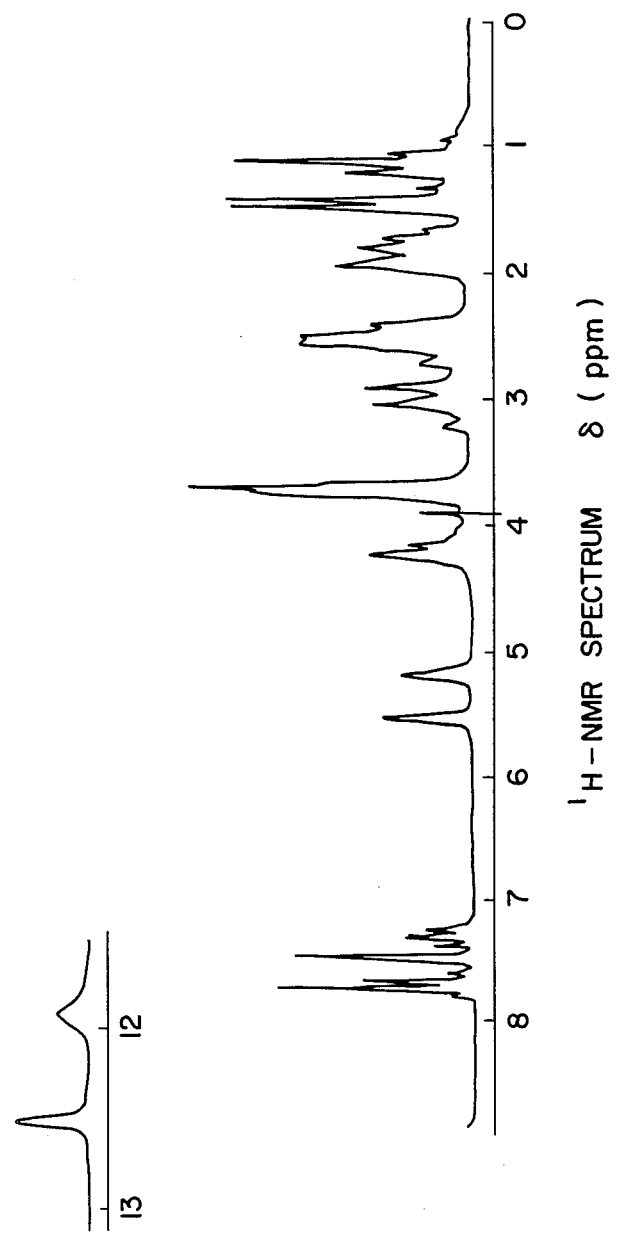
FIG. 9 is a graph showing the $^1$H-NMR spectrum of 3'-deamino-3'-(4-morpholinyl) R20Y5 in deuterochloroform.

(8) Proton NMR spectrum (100 MHz, in deuterochloroform): Shown in FIG. 9.

(9) Rf Value (on silica gel plate 60F$_{254}$ supplied by Merck & Co., Inc.):

| Solvent system | Rf Value |
|---|---|
| Chloroform:methanol (10:1) | 0.67 |
| Ethyl acetate:acetone (1:1) | 0.43 |

(10) Solubility: Soluble in acidic water, basic water, methanol, ethanol, propanol, acetone, ethyl acetate, chloroform, pyridine, and dimethyl sulfoxide but insoluble in water, hexane, cyclohexane, and diethyl ether.

PRODUCTION OF THE COMPOUNDS OF THE PRESENT INVENTION

I. Outline

The 3'-deamino-3'-(4-morpholinyl) derivatives of the present invention can be produced by synthetic chemical modification of R20 substances and R20Y5 obtained by the cultivation of microorganisms.

II. R20 Substances and R20Y5

The R20 substances and R20Y5 can be obtained from the culture of *Actinomadura roseoviolacea* 1029-AV1 (hereinafter referred to as "strain R20") isolated by us. The R20X can also be produced by the procedure described in West German Patent Application Laid-Open Pub. No. 3,012,665 as has been mentioned earlier, and the R20Y5 is a known substance which can also be produced by the procedure set forth in Japanese Patent Application Laid-Open Pub. No. 76896/1980 as has also been mentioned previously.

1. Strain R20

Strain R20, an anthracycline compound R20 substances- or R20Y5-producing strain of the genus Actinomadura discovered by us, will be described in detail below.

(1) Origin and Accession No.

Strain R20 is a Actinomadura strain isolated from the soil collected from a truck farm in Ohaza Onoya, Kahocho, Kaho-gun, Fukuoka-ken, Japan. This strain was deposited on July 5, 1983 with the Fermentation Research Institute, Agency of Industrial Sicence and Technology, Ministry of International Trade and Industry of Japan, 1-3, Higashi 1 chome, Yatabe-machi, Tsukuba-gun, Ibaraki-ken 305, Japan, where it was assigned the accession number FERM-P No. 7138. This strain now bears the accession number FERM BP-945 under the terms of the Budapest Treaty on the International Recognition of the Deposit of Microorganisms for the Purposes of Patent Procedure. This depository fully complies with the rules of the Budapest Treaty. Specifically, it fully complies with Rule 11.3 of the Budapest Treaty whereby the organism is available to the public on patent grant and with Rule 9 of the Budapest Treaty which requires the maintenance of the organism for a period of at least 30 years after the date of deposit.

(2) Microbiological characteristics and physiological properties

The taxonomic characteristics of strain R20 will be set forth below in accordance with the method adopted by ISP (International Journal of Systematic Bacteriology 16, pp. 313–340(1966)).

A. Morphology

Substrate mycelia of strain R20 are branched while extending radially over the surface of an agar medium, and no fragmented hyphae are observed. Aerial hyphae extend their main axis far, ramifying into short branches substantially perpendicular to the main axis (monopodial branching) and forming at the ends of the branches tightly closed spiral spore chains (1 to 3 turns, 2.0 to 2.5μ in diameter) consisting of about 10 or more spores, and pseudosporangia (2.5 to 3.5μ in diameter) or spore masses.

The chain of spores is covered with a cylindrical sheath of a width of 0.5 to 0.8μ having a rough surface, and the spores are connected with each other like phalanxes. The spore mass is amorphous, and the surface of each spore is covered with a slimy substance. Free spores, which are seldom observed, are of a cylindrical or elliptical shape, 0.5 to 0.8μ in width, 0.7 to 1.1μ in length, and have a smooth surface. No sporangia, flagellar spores or sclerotia are observed. In view of the fact that the whole cell hydrolyzate contains mesodiaminopimelic acid and madurose, the cell wall type is classified as type IIIB (Lechevalier, M. P. & Lechevalier, H. A., International Journal of Systematic Bacteriology 20 p. 435 (1970)).

B. Cultural characteristics

The results obtained by the observation of cultural characteristics of strain R20 cultivated on various culture media (at 27° C.) are as summarized in Table 1.

C. Physiological properties

The physiological properties (including carbon utilization) are as set forth in Table 2.

D. Discussion and identification

Strain R20 has been identified as an Actinomadura strain from the findings that (1) the cell wall is of type IIIB, (2) the spore chain consists of 10 or more spores, (3) pseudosporangia or spore masses are formed, and (4) no sporangia or flagellar spores are observed. According to the Nonomura's classification (Journal of Fermentation Technology 52, pp. 71–77, 1974) and description (ibid. 49, pp. 904–912, 1971), strain R20 is considered to be most closely analogous to A. roseoviolacea.

Strain R20 and a standard A. roseoviolacea strain [KCC A-145 (Nonomura A-5)] were cultivated under the same conditions to compare the principal properties of these strains. As will be noted from Table 3, the two strains are closely analogous to each other in view of taxonomy although there are slight differences in aerial mass color, reverse side pigment and optimum growth temperature.

Accordingly, strain R20 was identified as *Actinomadura roseoviolacea*, Nonomura et Ohara, 1971.

It is possible to further induce from this strain a mutant strain highly capable of producing R20 substances or R20Y5 in accordance with conventional microorganism mutating methods such as physical treatment by UV-ray, X-ray or γ-ray irradiation or chemical treatment with reagents such as nitrosoguanidine. It is also possible to induce R20 substances- or R20Y5-producing microorganisms by gene manipulation procedure, for example, by incorporating the gene DNA of the above strain which bears genetic information as to the production of R20 substances or R20Y5 into an appropriate vector which is in turn transferred by way of transformation into a microorganism of a genus other than Actinomadura, or by permitting the gene DNA to be taken up in a microorganism of another genus by cell fusion. It is to be understood that these microorganisms induced from the above strain are also included within the scope of the present invention.

TABLE 1

| Medium | Cultural characteristics | Color |
|---|---|---|
| Sucrose-nitrate agar | Aerial mass color | Red color series (pinkish white) |
| | Reverse side pigment | Pinkish gray, later pale reddish purple |
| | Soluble pigment | Pinkish white |
| Glucose-asparagine agar | Aerial mass color | Red color series (pinkish white-pale purplish pink-pink) |
| | Reverse side pigment | Light orange-dark orange, later dull red-dark red |
| | Soluble pigment | None |
| Glycerol-asparagine agar | Aerial mass color | Red color series (pale pink-slightly reddish purple) |
| | Reverse side pigment | Light yellowish orange, later bright yellow-dull yellowish orange |
| | Soluble pigment | Slight, pinkish |
| Inorganic salts-starch agar | Aerial mass color | Red color series (pale pink, later pale purplish pink) |
| | Reverse side pigment | Light orange-dark orange |
| | Soluble pigment | None |
| Tyrosine agar | Aerial mass color | No aerial hyphae formed |
| | Reverse side pigment | Light yellowish brown, later grayish yellowish brown |
| | Soluble pigment | None |
| Nutrient agar | Aerial mass color | No aerial hyphae formed |
| | Reverse side pigment | Dark reddish purple-light brown |
| | Soluble pigment | Slightly reddish brown, later light brownish gray |
| Yeast extract-malt extract agar | Aerial mass color | Red color series (pale purplish pink) |
| | Reverse side pigment | Deep reddish purple-dark reddish purple; turns orange when acidic and purple when basic |
| | Soluble pigment | Light brownish gray; turns purple when basic |
| Oatmeal agar | Aerial mass color | Red color series (pinkish white, later pale pink) |

TABLE 1-continued

| Medium | Cultural characteristics Color | |
|---|---|---|
| | Reverse side pigment | Pale reddish purple-dark reddish purple, later reddish orange-dark purplish red |
| | Soluble pigment | Light purplish gray |

TABLE 2

| Physiological Properties | |
|---|---|
| Growth temp. range | 25–45° C. |
| Optimum temp. | 27–30° C. |
| Production of melanoid pigment | |
| Tyrosine agar medium | − |
| Peptone-yeast extract-iron agar medium | − |
| Tryptone-yeast extract broth | − |
| Hydrolysis of starch | − |
| Liquefaction of gelatin | − |
| Coagulation of skim milk | − |
| Petonization of skim milk | + |
| Nitrate reduction | + |
| Carbon utilization (Pridham and Gottlieb basal medium) | ++L-arabinose, D-xylose, D-glucose, D-fructose, i-inositol, L-rhamnose +Sucrose, D-mannitol ±Raffinose |

TABLE 3

| Comparison Between R20 and *A. roseoviolacea* KCC A-145 | | R20 | *A. roseoviolacea* KCC A-145 |
|---|---|---|---|
| Glycerol-asparagine agar | Aerial mass color | Pale pink-slightly reddish purple | Pale pink-slightly reddish purple |
| | Reverse side pigment | Grayish reddish purple | Grayish reddish purple |
| | Soluble pigment | Slight, pinkish | Slight, pinkish |
| Inorganic salts-starch agar | Aerial mass color | Pale pink | Pale pink |
| | Reverse side pigment | Pink | Pale orange-pale pink |
| | Soluble pigment | None | None |
| Yeast extract-malt extract agar | Aerial mass color | Pale pink | Pale reddish purple |
| | Reverse side pigment | Dark reddish purple | Dark reddish purple |
| | Soluble pigment | Light orange-light reddish orange | Light orange-light reddish orange |
| Oatmeal agar | Aerial mass color | Pale reddish purple | Pale reddish purple |
| | Reverse side pigment | Reddish purple | Light reddish purple |
| | Soluble pigment | Pale reddish purple | Pale reddish purple |
| Morphology: | | | |
| Spore chain | | Tightly closed spiral | Tightly closed spiral |
| Pseudosporangium | | Many | Many |
| Optimum growth temperature | | 27–30° C. | 30–40° C. |
| Production of Melanoid pigment[1] | | − | − |
| Carbon utilization[2] | | Utilizable except raffinose (±) | Utilizable except raffinose (±) |
| Hydrolysis of starch | | − | − |
| Nitrate reduction | | Strongly positive | Strongly positive |

(Notes)
[1] The three types of culture media shown in Table 2.
[2] The nine types of saccharides shown in Table 2.

2. Cultivation for production of R20 substances or R20Y5

The anthracycline R20 substances or R20Y5 can be prepared by cultivating an R20 substances- or R20Y5-producing Actinomadura strain aerobically in a suitable medium and recovering the objective product from the culture.

Culture media may be those containing any nutrient sources which can be utilized by R20 substances- or R20Y5-producing strain. For example, glucose, sucrose, maltose, starch, oils and fats are useful as carbon sources. Exmples of nitrogen sources are organic materials such as soybean meal, cotton seed meal, meat extract, peptone, dry yeast, yeast extract and cornsteep liquor, and inorganic materials such as ammonium salts and nitrates (e.g., ammonium sulfate, sodium nitrate and ammonium chloride). If necessary, inorganic salts such as sodium chloride, potassium chloride, phosphates, and salts of heavy metals can also be added. In order to prevent foaming during fermentation, suitable antifoaming agents such as silicone may be added by a conventional method.

The most suitable method of cultivation is submerged aerobic liquid cultivation which is employed widely for the production of antibiotics. A suitable cultivation temperature is 25° to 45° C., preferably 27° to 30° C. In accordance with this method, the production output of the R20 substances or R20Y5 reaches a maximum after 6 to 7 days of shake culture or cultivation under aeration and stirring.

A culture in which R20 substances or R20Y5 is accumulated can thus be obtained. In the resulting culture a part of the R20 substances or R20Y5 is present in the mycelial cake while a greater part thereof is present in the filtrate of the culture.

The R20 substances or R20Y5 can be recovered from the culture by any method suitable for the recovery. One such method is based on extraction. For example, the R20 substances or R20Y5 in the filtrate of the culture can be recovered by extraction with a water-immiscible solvent for R20 substances or R20Y5 such as ethyl acetate, chloroform, or butanol. (A high extraction efficiency is achieved when the culture filtrate is neutral or weakly basic.) The R20 substances or R20Y5 in the mycelial cake can be recovered by treating the cells, which have been obtained by filtration or centrifugation, with chloroform, ethyl acetate, butanol, methanol, ethanol, acetone, a hydrochloric acid solution, or an acetic acid solution. It is also possible to subject the culture as such to the above-mentioned extraction procedure without preliminarily isolating the mycelial cake. Countercurrent distribution using a suitable solvent may be included in the extraction methods.

Another method for recovering the R20 substances or R20Y5 from the culture is based on adsorption. An R20 substances- or R20Y5-containing liquid material, such as a culture filtrate or an extract obtained by the extraction procedure described hereinbefore, is subjected, for example, to column chromatography including liquid chromatography using a suitable adsorbent, such as activated carbon, alumina, silica gel or "Diaion HP20" (supplied by Mitsubishi Kasei K.K., Japan). The desired R20 substances or R20Y5 adsorbed onto the adsorbent is then eluted therefrom. The resulting R20 substances or R20Y5 solution is concentrated to dryness under reduced pressure to obtain a crude product of R20 substances or R20Y5.

The crude R20 substance product can be separated into R20X and R20X2 and purified, or the crude R20Y5 product can be purified by carrying out the aforementioned extraction or adsorption procedure, if necessary, in combination, over a necessary number of times, followed by recrystallization, as necessary. For example, purification can be accomplished by an appropriate combination of column chromatography using an adsorbent or a gel filter such as silica gel, a weakly acidic ion exchange resin or activated carbon; liquid chromatography using a suitable solvent; and countercurrent distribution. A specific example of the purification method comprises dissolving the crude R20 substance or R20Y5 product in a small quantity of chloroform, applying the solution to a silica gel column, and developing the column with a suitable solvent to elute the active component of the R20 substances or R20Y5. The eluate is concentrated under reduced pressure, further developed on TLC, and scraped off the TLC. By the elution from the scraped fraction, R20X and R20X2 are respectively isolated as single substances in the former case while R20Y5 is isolated as a single substance in the latter case. These substances are concentrated to dryness, whereby R20X and R20X2 or R20Y5 can be obtained.

The R20 substances or R20Y5 thus obtained has physicochemical properties as shown in Table 4 below. The data for F20Y5 coincide with the physicochemical properties set forth in Japanese Patent Application Laid-Open Pub. No. 76896/1980.

TABLE 4

Physicochemical Properties of R20 Substances and R20Y5

Figure 10:
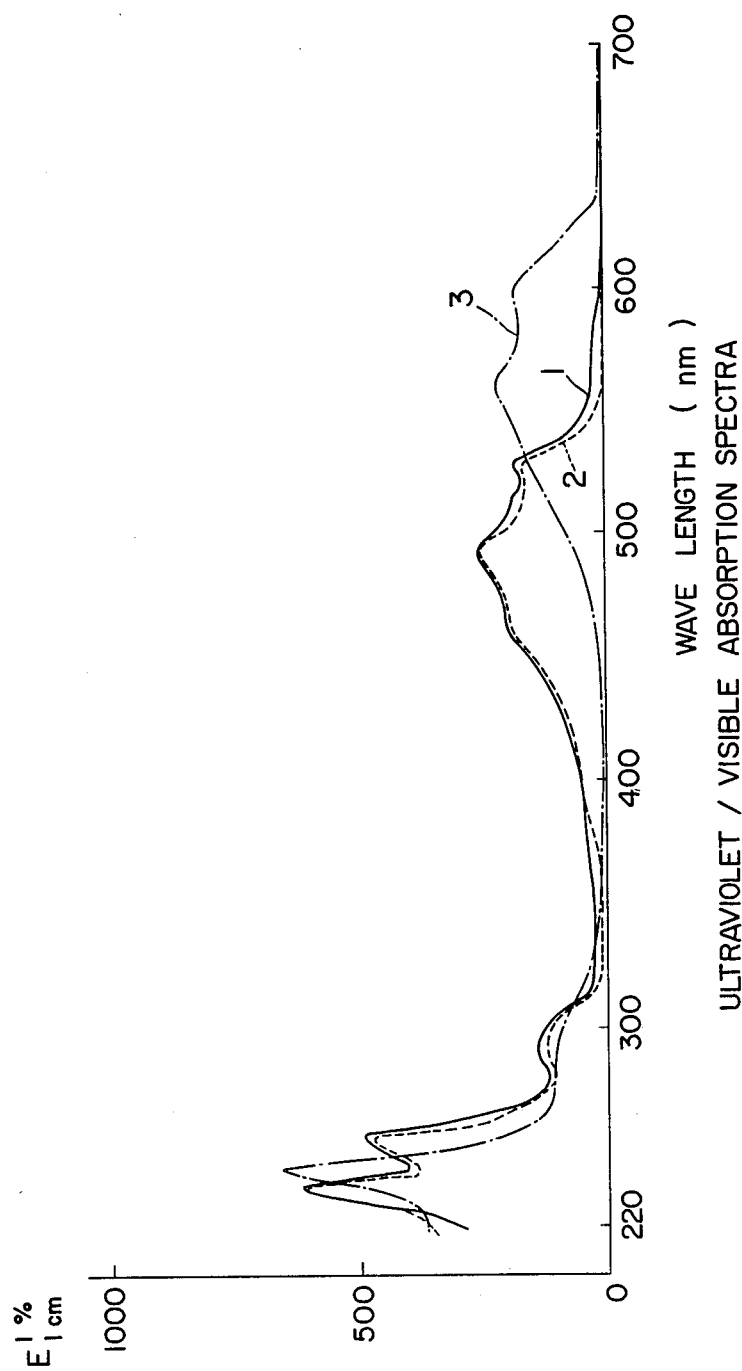
FIG. 10 is a graph showing the ultraviolet/visible absorption spectra of R20X, the curve 1 showing the spectrum in methanol, the curve 2 the spectrum in methanol plus 0.1N HCl, and the curve 3 the spectrum in methanol plus 0.1N NaOH.
Figure 11:
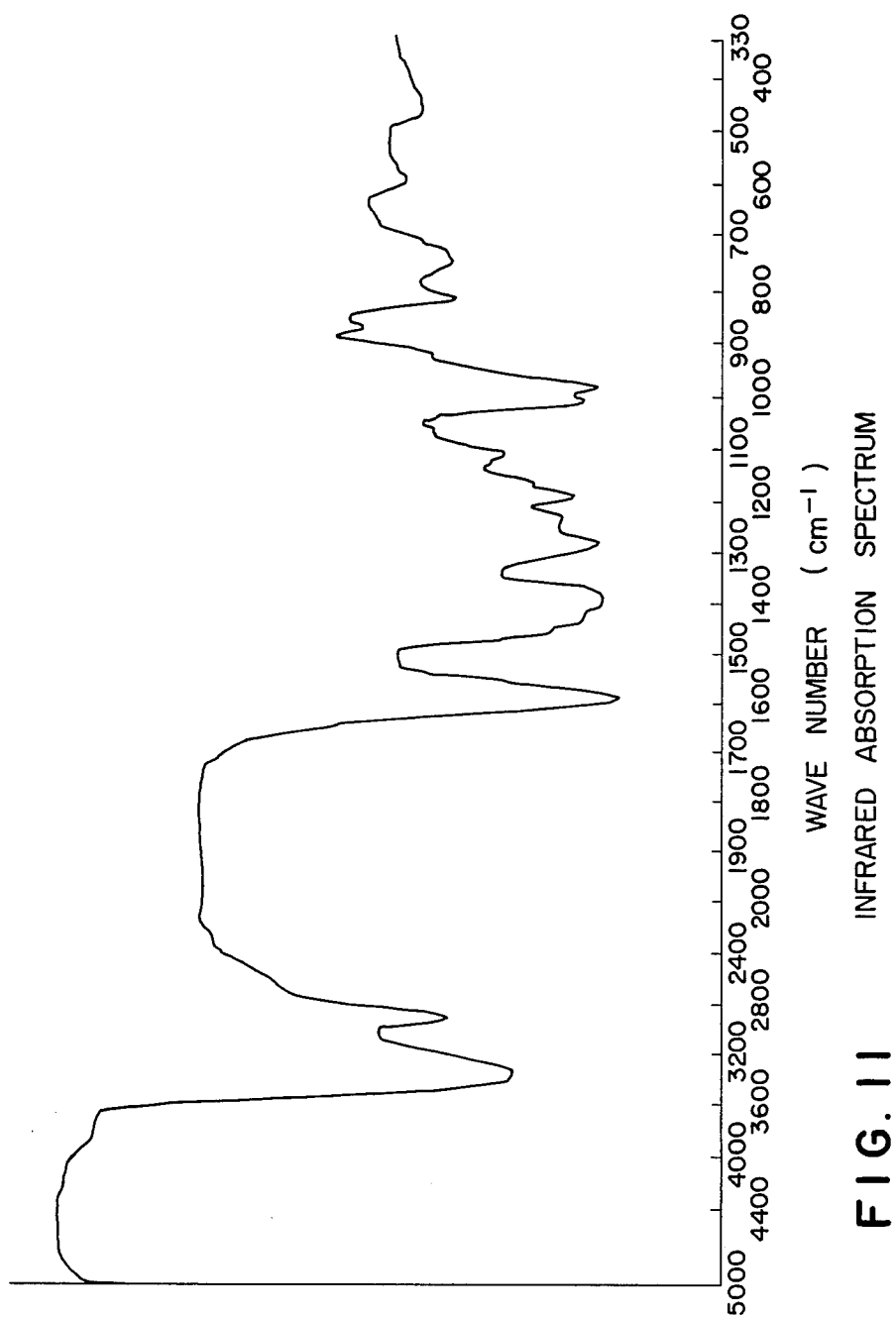
FIG. 11 is a graph showing the infrared absorption spectrum of R20X.
Figure 12:
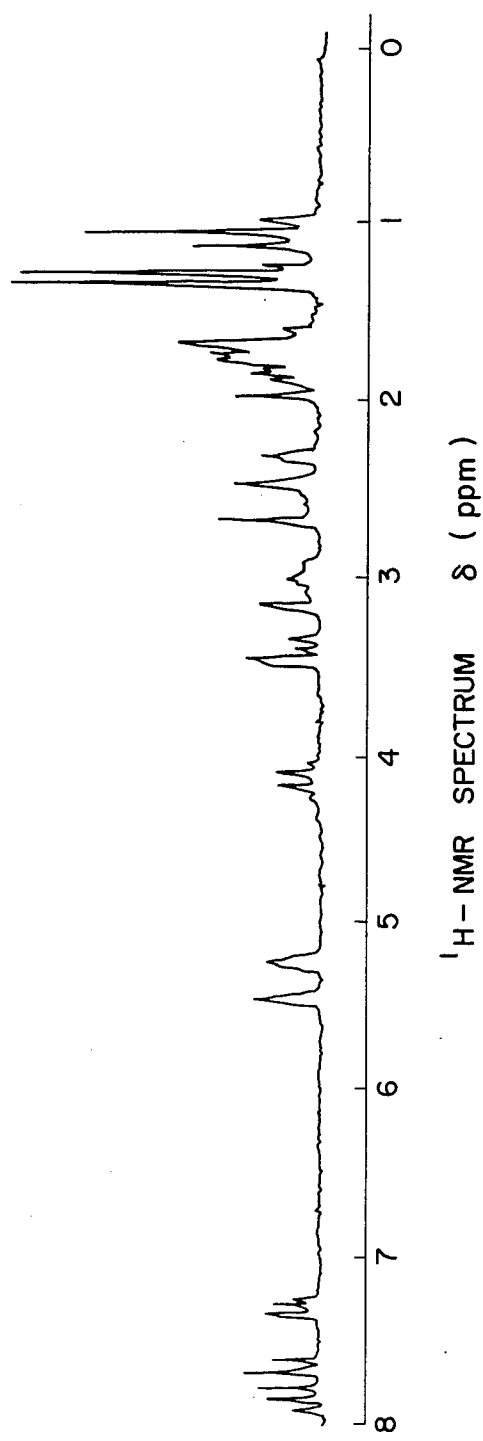
FIG. 12 is a graph showing the $^1$H-NMR spectrum of R20X in deuterochloroform.
Figure 13:
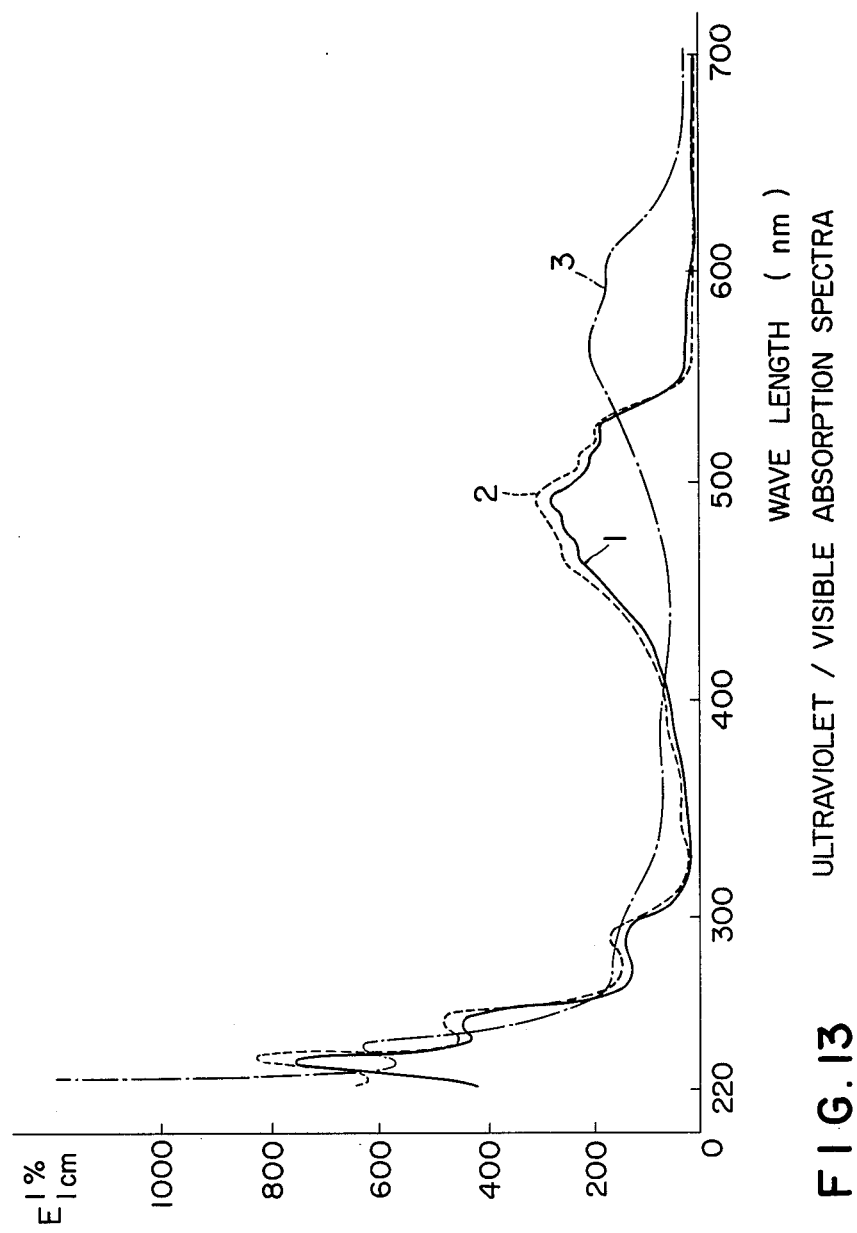
FIG. 13 is a graph showing the ultraviolet/visible absorption spectra of R20X2, the curve 1 showing the spectrum in methanol, the curve 2 the spectrum in methanol plus 0.1N HCl, and the curve 3 the spectrum in methanol plus 0.1N NaOH.
Figure 14:
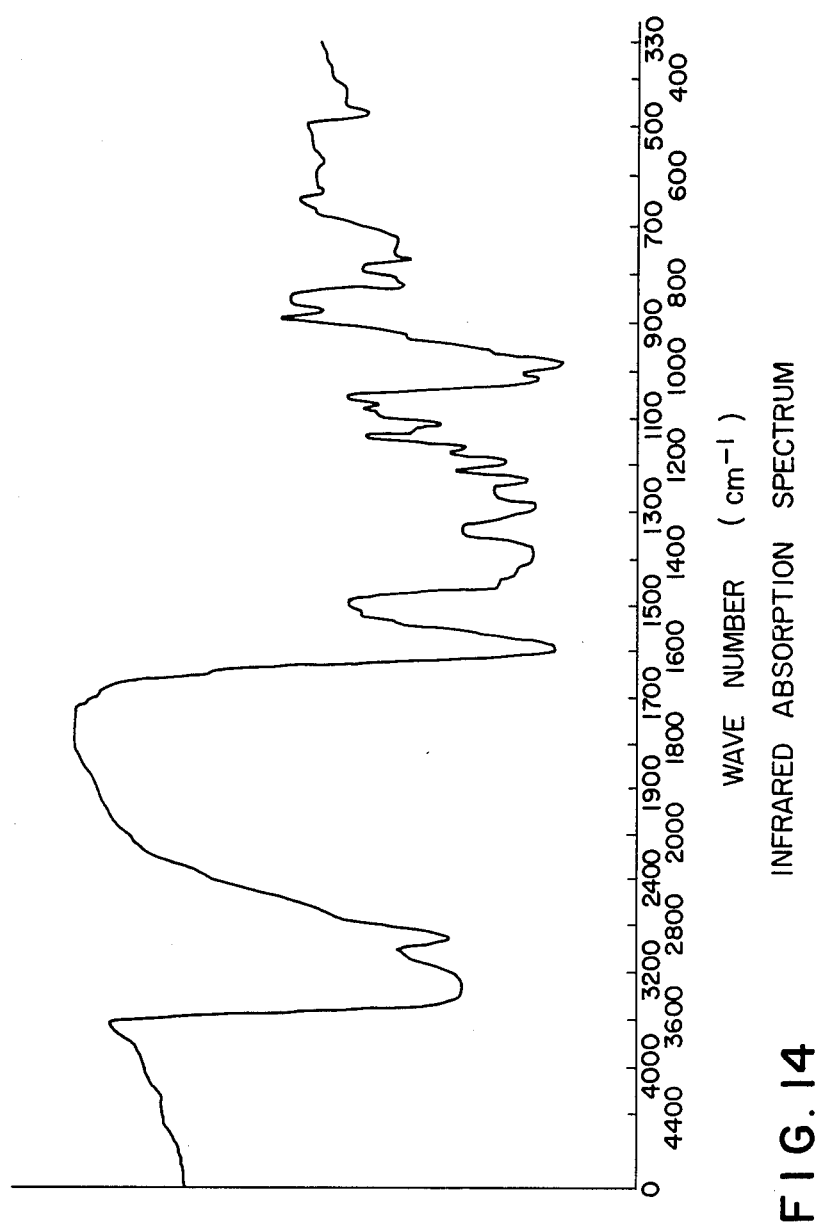
FIG. 14 is a graph showing the infrared absorption spectrum of R20X2.
Figure 15:
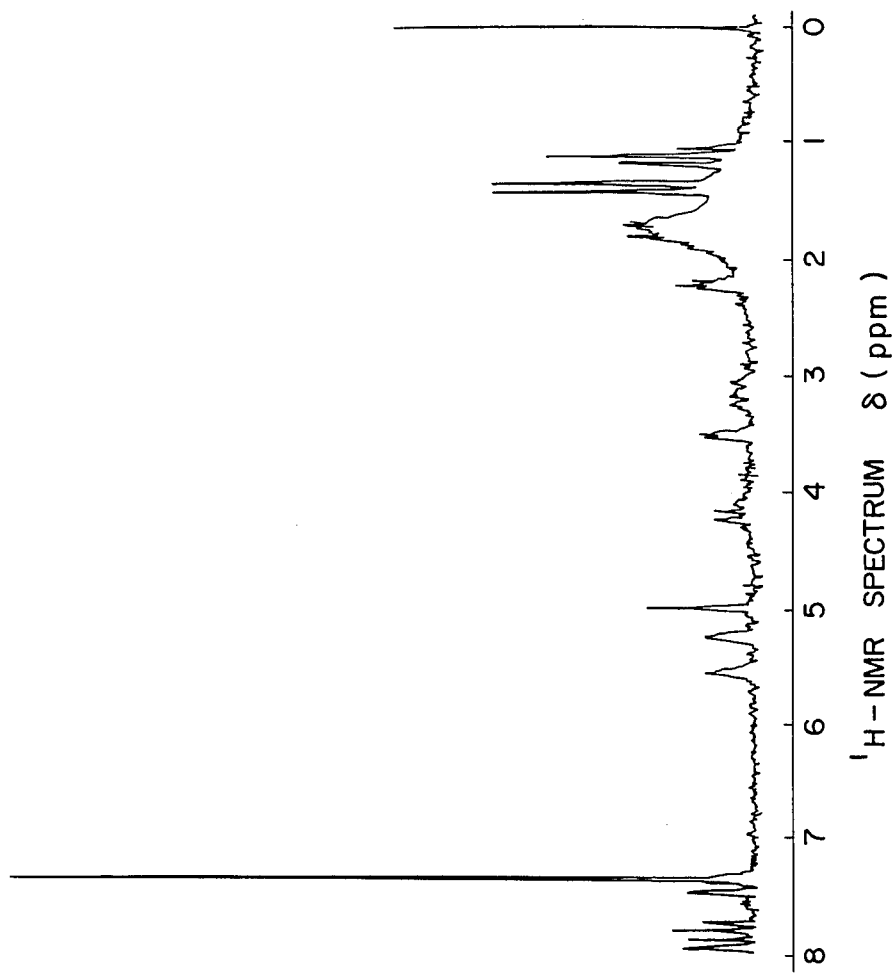
FIG. 15 is a graph showing the $^1$H-NMR spectrum of R20X2 in deuterochloroform.
Figure 16:
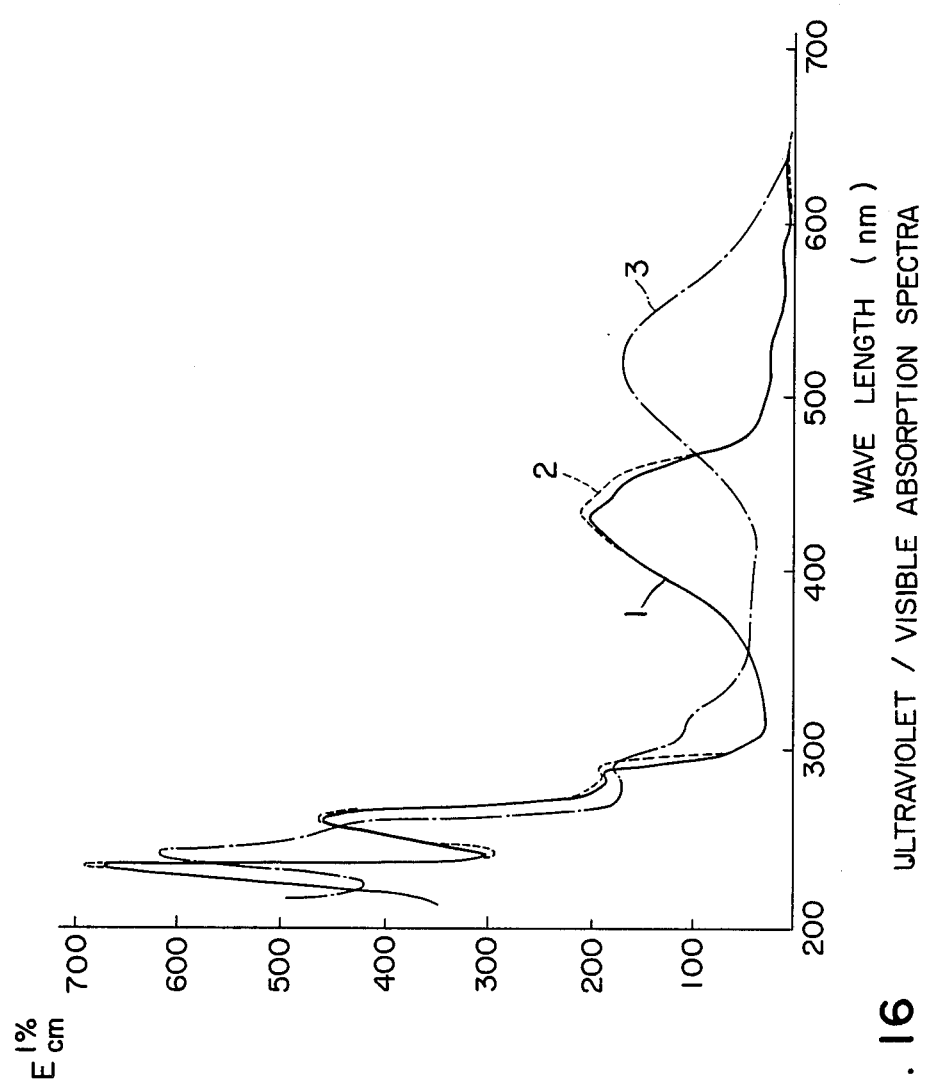
FIG. 16 is a graph indicating the ultraviolet/visible absorption spectra of R20Y5, the curve 1 indicating the spectrum in methanol, the curve 2 the spectrum in methanol plus 0.1N HCl, and the curve 3 the spectrum in methanol plus 0.1N NaOH.
Figure 17:
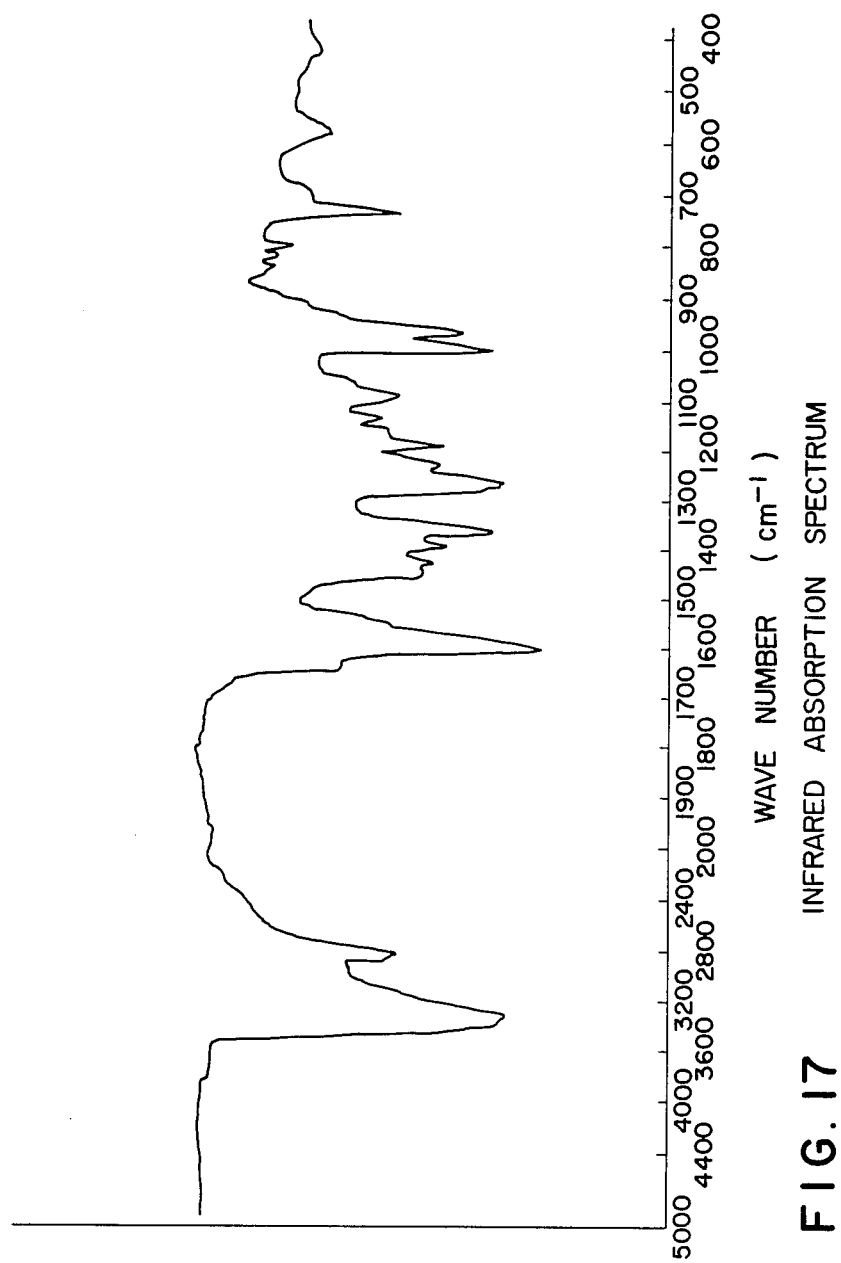
FIG. 17 is a graph indicating the infrared absorption spectrum of R20Y5.
Figure 18:
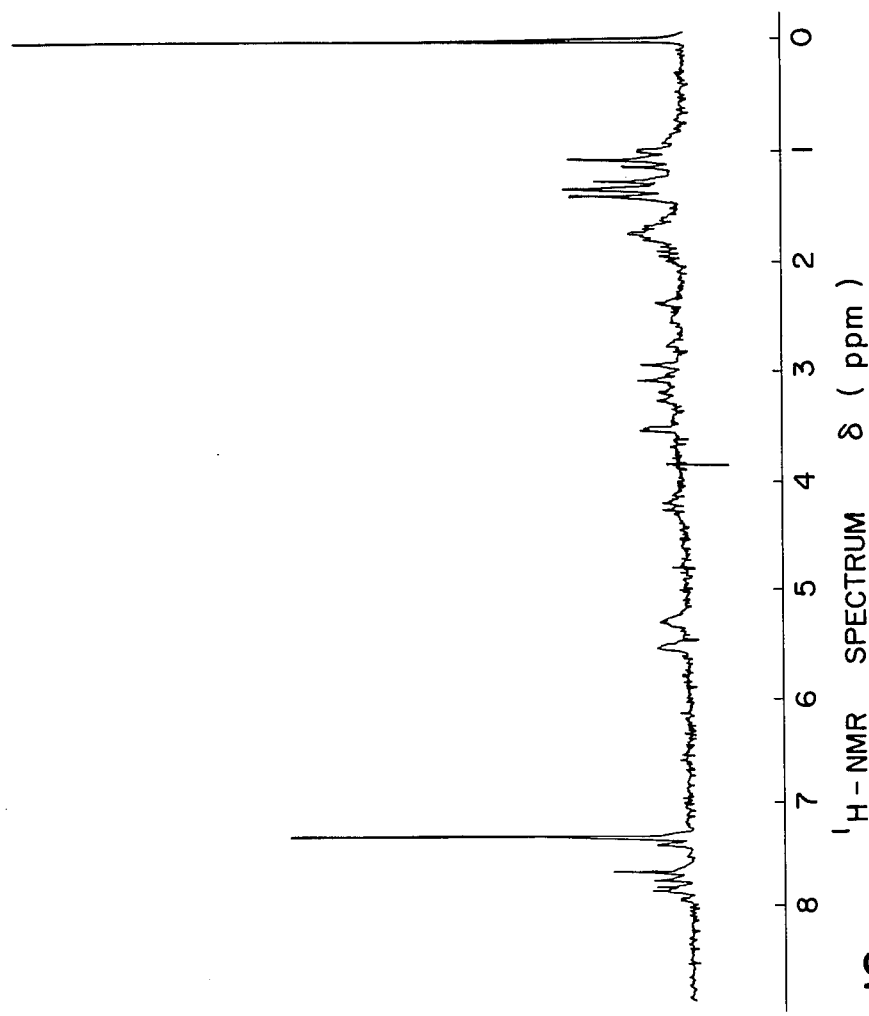
FIG. 18 is a graph indicating the $^1$H-NMR spectrum of R20Y5 in deuterochloroform.

| No. | Properties | R20X | R20X2 | R20Y5 |
|---|---|---|---|---|
| 1 | Color & Form | Dark brown powder | Dark brown powder | Yellowish brown powder |
| 2 | Elementary analysis (%) | C  H  N  O | C  H  N  O | C  H  N  O |
|  | Found | 61.83  5.99  2.76  29.42 | 60.45  5.77  2.66  31.12 | 63.82  6.32  2.82  27.04 |
|  | Calcd. | 62.52  5.85  2.80  28.83 | 60.58  5.67  2.72  31.03 | 64.59  6.05  2.90  26.47 |
| 3 | Molecular weight | 499 (FD-MS), Molecular formula: $C_{26}H_{29}O_9N$ | 515 (FD-MS), Molecular formula: $C_{26}H_{29}O_{10}N$ | 483 (FD-MS), Molecular formula: $C_{26}H_{29}O_8N$ |
| 4 | Melting point | 131–134° C. (decomposed) | 112–115° C. | 148–153° C. |
| 5 | Specific rotatory power $[\alpha]_D^{25}$ | +258° (C = 0.05 in methanol) | +263° (C = 0.1 in $CHCl_3$:MeOH = 1:1) | +187.2° (C = 0.125 in methanol) |
| 6 | UV & visible absorption spectrum $\lambda_{max}$ nm ($E_{1cm}^{1\%}$) | FIG. 10 | FIG. 13 | FIG. 16 |
| 7 | IR absorption spectrum (KBr method) | FIG. 11 | FIG. 14 | FIG. 17 |
| 8 | Proton NMR spectrum (100 MHz, in deuterochloroform) | FIG. 12 | FIG. 15 | FIG. 18 |
| 9 | Solubility | Soluble: acidic water, basic water, methanol, ethanol, propanol, acetone, ethyl acetate, chloroform  Insoluble: water, hexane, cyclohexane, diethyl ether, petroleum ether | Soluble: acidic water, basic water, methanol, ethanol, n-propanol, acetone, ethyl acetate, chloroform  Insoluble: water, hexane, cyclohexane, diethyl ether, petroleum ether (brown in methanol, but turns bluish purple in an alkaline state) | Soluble: acidic water, basic water, methanol, ethanol, propanol, acetone, ethyl acetate, chloroform, pyridine, dimethyl sulfoxide, water  Insoluble: hexane, cyclohexane, diethyl ether |
| 10 | Rf value (on silica gel plate 60F254 supplied by Merck & Co., Inc.) | 0.24 chloroform:methanol:water = 8:2:0.05  0.33 chloroform:methanol:acetic acid = 8:2:0.05  0.46 chloroform:methanol:ammonia water = 8:2:0.05 | 0.16 chloroform:methanol:water = 8:2:0.05  0.26 chloroform:methanol:acetic acid = 8:2:0.05  0.44 chloroform:methanol:ammonia water = 8:2:0.05 | 0.50 chloroform:methanol:acetic acid:water = 40:8:1:1 |

III. Synthetic chemical modification of R20 substances and R20Y5.

The 3'-deamino-3'-(4-morpholinyl) derivatives of the present invention can be prepared by the method which involves reacting R20 substances or R20Y5 or an acid addition salt thereof with the compound of the formula (IV) (hereinafter referred to as "method A") or by the method which involves reacting R20 substances or R20Y5 or an acid addition salt thereof with bis-(2-haloethyl)ether of the formula (V) in the presence of a dehydrohalogenating agent (hereinafter referred to as "method B").

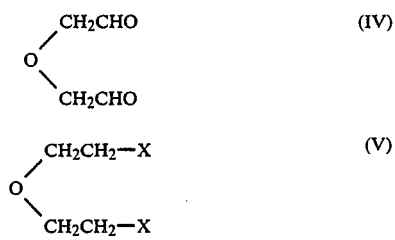

wherein X is a bromine atom or iodine atom.

In the method A, the compound (IV) can be obtained from mesoerythritol by the procedure described in literature (Carbohydrate Research 35 pp. 195–202 (1974)).

The reaction of R20 substances or R20Y5 or an acid addition salt thereof with the compound of the formula (IV) is ordinarily carried out in a solvent. Examples of solvents which can be used for the reaction are acetonitrile, methanol, ethanol, water, chloroform, dichloromethane, carbon tetrachloride, benzene, dioxane, and tetrahydrofuran, singly or in a mixture of two or more members, a solvent mixture of acetonitrile, water and chloroform being especially preferred.

This reaction is desirably carried out in the presence of a reducing agent such as sodium borohydride ($NaBH_4$) or sodium cyanoborohydride ($NaBH_3CN$). The quantity of the reducing agent used is not critical, and the agent can be used in a quantity of at least 1 mol, preferably 1 to 5 mols, per mol of R20 substances or R20Y5.

The compound of the formula (IV) is advantageously used in a quantity of at least 1.5 mol, preferably at least 5 mols, and more preferably 8 to 15 mols, per mol of R20 substances or R20Y5.

A suitable reaction temperature is generally in the range of from the solidifying point of the solvent employed to 50° C., a temperature around room temperature being particularly suitable.

Under the above stated reaction conditions, the reaction of converting the amino group into the morpholinyl group can be terminated within about 10 min. to 2 hours.

In the method B, R20 substances or R20Y5 or an acid addition salt thereof is reacted with a compound of the formula (V) in the presence of a dehydrohalogenating agent under essentially the same conditions as are disclosed in Japanese Pat. Appln. Laid-Open Pub. No. 163393/1982. It is noteworthy with respect to this method B that, when R20X2 and R20Y5 are subjected to the above reaction, the corresponding 3'-deamino-3'-(4-morpholinyl) derivatives are respectively obtained while, when R20X is subjected to the same reaction, 3'-deamino-3'(4-morpholinyl) derivatives corresponding to both R20X and R20X2 are obtained simultaneously (cf. Example 6).

The reaction mixture obtained by the reaction of the R20 substances or R20Y5 or an acid addition salt thereof with the compound of the formula (IV) or a compound of the formula (V) according to the method of the present invention can be purified to isolate a desired compound, a 3'-deamino-3'-(4-morpholinyl) derivative, by a known purification procedure employed in the preparation of glycoside derivatives of anthracycline compound, for example, chromatography using silica gel and the like.

The 3'-deamino-3'-(4-morpholinyl) derivatives of the formula (I) thus obtained themselves can be converted into acid addition salts thereof by a known method, for example, by treating the derivatives with inorganic acids such as hydrochloric acid, sulfuric acid and phosphoric acid or organic acids such as acetic acid, propionic acid, maleic acid, oleic acid, palmitic acid, citric acid, succinic acid, tartaric acid, fumaric acid, glutamic acid, pantothenic acid, and laurylsulfonic acid.

USES OF THE COMPOUNDS OF THE PRESENT INVENTION

The novel anthracycline compounds according to the present invention have a remarkable carcinostatic activity as well as a high therapeutic index and thus are useful as medicines.

(I) Physiological activities
(1) Antitumor activity
a. Antitumor activity against leukemia The 3'-deamino-3'-(4-morpholinyl) derivatives of the present invention exhibited outstanding antitumor activity against leukemia of subject animals. For instance, into $CDF_1$ mice were intraperitoneally transplanted P388 leukemia $1 \times 10^6$ cells/mouse as a suspension, and the 3'-deamino-3'-(4-morpholinyl) derivatives were intraperitoneally administered to the mice 1 day and 5 days respectively after the transplantation. The mice were observed for 30 days, and the effect of the test compounds was determined in terms of T/C (%), the survival days of the control mice which had been administered with physiological saline solution instead of the test compounds being specified as 100. Presented in Table 5 are the data so obtained. Also presented in the same table are the therapeutic indices (maximum tolerated dose/dose for 130% T/C) which indicate effectiveness of the test compounds in clinical therapy.

TABLE 5

| | T/C and therapeutic index in the case of i.p. administration | | | | |
|---|---|---|---|---|---|
| | Compound | | | | |
| Dose (mg/kg/day) | 3'-deamino-3'-(4-morpholinyl)-R20X | 3'-deamino-3'(4-morpholinyl)-R20X2 | 3'-deamino-3'-(4-morpholinyl)-R20Y5 | Adriamycin (comp. data) | Aclacinomycin (comp. data) |
| T/C (%) 0.25 | — | 112 | — | 148 | — |
| 0.5 | 104 | 150 | — | 177 | — |
| 1 | 148 | 186 | — | 191 | — |
| 2 | 177 | >246 | — | >217 | 111 |
| 4 | 218 | >158 | 104 | 204 | 126 |

TABLE 5-continued

T/C and therapeutic index in the case of i.p. administration

| Dose (mg/kg/day) | 3'-deamino-3'-(4-morpholinyl)-R20X | 3'-deamino-3'(4-morpholinyl)-R20X2 | 3'-deamino-3'-(4-morpholinyl)-R20Y5 | Adriamycin (comp. data) | Aclacinomycin (comp. data) |
|---|---|---|---|---|---|
| 8 | >303 | — | 146 | >256 | 155 |
| 12 | 231* | — | — | 194 | — |
| 16 | — | — | 175 | — | 182 |
| 32 | — | — | 219 | — | — |
| 64 | — | — | 93 | — | — |
| Dose for T/C = 130 % (mg/kg/day) | 0.75 | 0.35 | 6.2 | <0.25 | 4.4 |
| Therapeutic index | 10.7 | 5.7 | 5.2 | >32 | 3.6 |

*administered only day 1

Further, into CDF$_1$ mice were intraperitoneally transplanted P 388 leukemia $1\times10^6$ cells/mouse as a suspension, and the 3'-deamino-3'-(4-morpholinyl) derivatives were intravenously administered to the mice 1 day and 5 days respectively after the transplantation. The mice were observed for 30 days, and the effect of the test compounds was determined in terms of T/C (%), the survival days of the control mice which had been administered with physiological saline solution instead of the test compounds being specified as 100. The results obtained are shown in Table 6 below together with the therapeutic indices of the compounds.

TABLE 6

T/C and therapeutic index in the case of i.v. administration

| Dose (mg/kg/day) | | 3'-deamino-3'-(4-morpholinyl)-R20X | 3'-deamino-3'-(4-morpholinyl)-R20X2 | 3'-deamino-3'(4-Morpholinyl)-R20Y5 | Adriamycin (comp. data) | Aclacinomycin (comp. data) |
|---|---|---|---|---|---|---|
| T/C (%) | 0.25 | — | 109 | — | — | — |
| | 0.5 | — | 136 | — | — | — |
| | 1 | 104 | 154 | — | 103 | — |
| | 2 | 119 | 204 | 104 | 119 | — |
| | 4 | 155 | 194 | 123 | 133 | 121 |
| | 8 | 151 | 35* | 148 | 165 | 119 |
| | 12 | 57 | — | — | 224 | — |
| | 16 | — | — | 182 | — | 151 |
| | 32 | — | — | >240 | — | 177 |
| | 64 | — | — | — | — | 35* |
| Dose for T/C = 130% (mg/kg/day) | | 2.5 | 0.43 | 4.9 | 3.5 | 12.4 |
| Therapeutic index | | 1.6 | 4.7 | 6.5 | 3.4 | 2.6 |

*administered only day 1

Furthermore, into CDF$_1$ mice were intraperitoneally transplanted P 388 leukemia $1\times10^6$ cells/mouse as a suspension, and the 3'-deamino-3'-(4-morpholinyl) derivatives were orally administered to the mice 1 day and 5 days respectively after the transplantation. The mice were observed for 30 days, and the effect of the test compounds was determined in terms of T/C (%), the survival days of the control mice which had been administered with physiological saline solution instead of the test compounds being specified as 100. The results obtained are set forth in Table 7 together with the therapeutic indices of the compounds.

TABLE 7

T/C and therapeutic index in the case of oral oral administration

| Dose (mg/kg/day) | | 3'-deamino-3'-(4-morpholinyl)-R20X | 3'-deamino-3'-(4-morpholinyl)-R20X2 | 3'-deamino-3'-(4-morpholinyl)-R20Y5 | Aclacinomycin (comp. data) |
|---|---|---|---|---|---|
| T/C (%) | 0.25 | — | 109 | — | — |
| | 0.5 | — | 120 | — | — |
| | 1 | 111 | 164 | — | — |
| | 2 | 146 | 228 | — | — |
| | 4 | 170 | 103* | 127 | — |
| | 8 | 214 | — | 154 | 119 |
| | 12 | — | — | — | — |
| | 16 | 219 | — | 191 | 131 |
| | 32 | — | — | 263 | 154 |
| | 64 | — | — | 238 | — |
| Dose for T/C = 130% (mg/kg/day) | | 1.45 | 0.58 | 4.3 | 15 |
| Therapeutic index | | 11.0 | 3.4 | 7.4 | 2.1 |

*administered only day 1

Adriamycin, which is the strongest medicine among anthracycline-base antitumor agents, is effective when administered intravenously but is ineffective in the case of oral administration. On the other hand, Aclacinomycin, which is another example of this type of antitumor agents, is known to be effective in the case of oral administration.

In view of the data given in the above Tables, the novel anthracycline compounds of the present invention have been found to exhibit therapeutic effects comparable to or better than those of Adriamycin when administered intraperitoneally and intravenously, and also have been found to be more highly effective than Aclacinomycin even in the case of oral administration where Adriamycin is ineffective. For these reasons, the compounds of the present invention are considered to have very bright prospects as therapeutic agents.

It has also been found from the comparison between the antitumor effects of R20Y5 described in Japanese Patent Application Laid-Open Pub. No. 76896/1980, i.e., 11-deoxy-13-deoxo-carminomycin and the 3'-deamino-3'-(4-morpholinyl)-R20Y5 derivative of the present invention that the antitumor activity of R20Y5 can be remarkably increased by 3'-deamino-3'-4-morpholinylation.

b. Antitumor activity against solid tumors

The 3'-deamino-3'-(4-morpholinyl) derivatives of the present invention exhibited antitumor activity not only against leukemia but also against solid tumors of subject animals. For example, into C57BL mice were subcutaneously transplanted Lewis lung carcinoma, and a 3'-deamino-3'-(4-morpholinyl) derivative of the present invention was intravenously administered to the mice 1 day, 5 days and 9 days respectively after the transplantation. On day 13, the size of the tumor was measured, and the effect of the test compound was determined in terms of the tumor growth inhibition (%) which was calculated as follows:

Tumor growth inhibition (%) =

$$\left(1 - \frac{\text{tumor size of treated mice}}{\text{tumor size of control mice}}\right) \times 100$$

The results were as summarized in Table 8.

TABLE 8

| | Growth inhibition against solid tumors | |
|---|---|---|
| | Tumor growth inhibition (%) | |
| Dose (mg/kg/day) | 3'-deamino-3'-(4-morpholinyl)-R20Y5 | Adriamycin (comp. data) |
| 1 | — | 34.5 |
| 2 | — | 14.1 |
| 4 | 9.6 | 64.2 |
| 8 | 31.0 | 72.8 |
| 16 | 66.6 | — |
| 32 | 91.7 | — |

From the above data, the 3'-deamino-3'-(4-morpholinyl)-R20Y5 according to the present invention has also been found to have antitumor activity comparable to or better than that of Adriamycin against solid tumors.

Cytotoxic activity against Adriamycin-resistant tumor cells

The 3'-deamino-3'-(4-morpholinyl) derivatives of the present invention further exhibited cytotoxic activity against Adriamycin-resistant tumor cells similarly as against sensitive tumor cells. In one operation, Adriamycin-resistant P 388 leukemia cells (P 388/ADR) and sensitive P 388 leukemia cells (P 388/S) were respectively suspended in RPMI 1640 plus 10% FBS medium each in a ratio of $5 \times 10^4$ cells/ml. To the resulting suspensions were added diluted 3'-deamino-3'-(4-morpholinyl) derivatives of the present invention, and the cells were cultivated at 37° C. in 5% $CO_2$. On day 2 the number of cells was counted, and the test compounds were compared in respect of the inhibitory concentration of the compounds indicating the 50% cell number ($IC_{50}$) of the control suspension to which the compounds had not been added thereby to determine the efficacy of the test compounds. The results obtained are shown in the following Table 9.

TABLE 9

| | $IC_{50}$ (μg/ml) | | |
|---|---|---|---|
| Compound | P388/S | P388/ADR | R/S |
| 3'-deamino-3'-(4-morpholinyl)-R20X | 0.033 | 0.038 | 1.15 |
| 3'-deamino-3'-(4-morpholinyl)-R20X2 | 0.009 | 0.011 | 1.22 |
| 3'-deamino-3'-(4-morpholinyl)-R20Y5 | 0.10 | 0.15 | 1.50 |
| Aclacinomycin (comp. data) | 0.013 | 0.025 | 1.92 |
| Adriamycin (comp. data) | 0.012 | 0.35 | 29.2 |

(2) Toxicity a. Acute toxicity ($LD_{50}$ values)

$LD_{50}$ values of the 3'-deamino-3'-(4-morpholinyl) derivatives of the present invention by intravenous injection to ICR mice were as indicated below.

| Compound | $LD_{50}$ (mg/kg) |
|---|---|
| 3'-deamino-3'-(4-morpholinyl)-R20X | 12.3 |
| 3'-deamino-3'-(4-morpholinyl)-R20X2 | 3.55 |
| 3'-deamino-3'-(4-morpholinyl)-R20Y5 | 65 |
| R20Y5 (comp. data)* | 15 |

*The data is based on Japanese Patent Application Laid-Open Pub. No. 76896/1980.

b. Toxicity to the heart

One of the side effects of anthracycline-based antitumor agents, particularly Adriamycin, is toxicity to the heart. The 3'-deamino-3'-(4-morpholinyl) derivatives of the present invention were found to be less toxic to the heart than Adriamycin.

Figure 19:
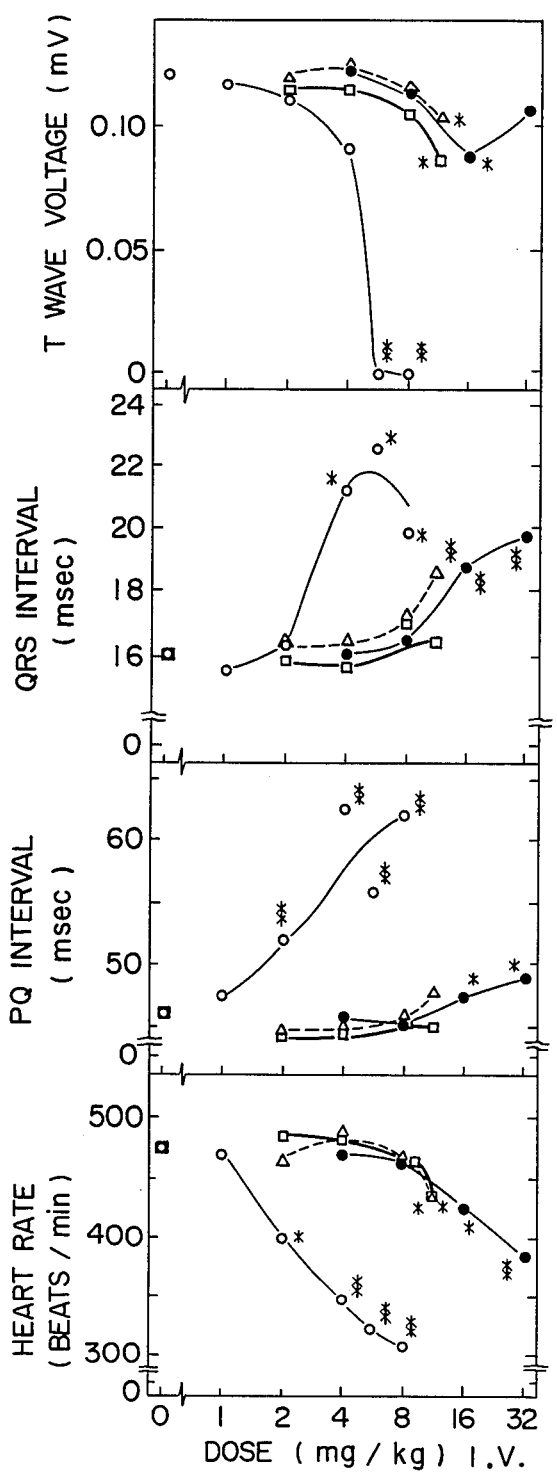
FIG. 19 shows graphs illustrating the effects of the 3'-deamino-3'-(4-morpholinyl) derivatives according to the present invention on the heart.

Golden hamsters anesthetized with urethane were administered via femoral veins with the respective 3'-deamino-3'-(4-morpholinyl) derivatives dissolved in physiological saline solution. The electrodes for electrocardiography were then inserted into the limbs of the hamsters to trace variations in electrocardiograms. The hamsters were subjected to electrocardiography 1 min. before the administration, and 0.5, 1, 3, 5, 10 and 15 min. respectively after the administration of the test compounds. Measured were T-wave potential (which is lowered by myocardiopathy), QRS interval (which is increased by aberrant ventricular conduction), PQ interval (which is increased by aberrant atrial conduction), and number of heart beats. The results are illustrated in FIG. 19.

The effect of the dosage level of all the novel anthracycline compounds of the present invention with respect to each of the above measurements was milder than that of Adriamycin, the toxicity being 1/6 or less as compared with Adriamycin on the point of dosage levels.

Adriamycin was found to be toxic to the heart at a dosage level at which the antitumor activity thereof starts to be exhibited (T/C=130%), while none of the compounds of the present invention was found to be toxic at this dosage level. Additionally, 3'-deamino-3'-(4-morpholinyl)-R20X and R20X2 were not found to be toxic even at a dosage level at which the maximum antitumor activity (T/C=max) thereof was exhibited.

II. Antitumor agent

As has been mentioned previously, the novel anthracycline compounds of the present invention were found to have antitumor activity against tumors, particularly malignant tumors in animals including humans.

Accordingly, the 3'-deamino-3'-(4-morpholinyl) derivatives of the present invention can be used as antitumor agents or pharmaceutical agents for treating tumors.

The 3'-deamino-3'-(4-morpholinyl) derivatives as antitumor agents can be administered via any route suited for the desired purpose in a dosage form determined by the route of administration. Ordinarily, the compounds diluted with pharmaceutically acceptable carriers or diluents are administered as drugs.

A typical method of administering the 3'-deamino-3'-(4-morpholinyl) derivatives as antitumor agents is by injection of solutions thereof in distilled water for injection use or in physiological saline. Examples of injection include intraperitoneal injection, subcutaneous injection, intravenous or intraarterial injection, and topical administration in case of animals; and intravenous or intraarterial injection and topical administration in case of humans.

The doses of the 3'-deamino-3'-(4-morpholinyl) derivatives are determined in view of the results of animal experiments and varying circumstances in such a manner that a total of doses given continuously or intermittently will not exceed a predetermined limit. Needless to say, particular doses required vary depending on the mode of administration; situations of subjects to be treated, such as age, body weight, sex, and susceptibility; food; times of administration; concomitant drugs; and conditions of subjects or severity of their diseases. The optimum doses and the frequency of administration under certain conditions must be determined by experts' optimum dose determination tests on the basis of the above-mentioned factors.

EXPERIMENTAL EXAMPLES

In the following examples, "%" is "w/v%".

EXAMPLE 1

Production of R20 substances (1) Inoculum Preparation

A medium used to grow a primary inoculum was prepared by dissolving the following ingredients in 1 liter of water and adjusting the pH of the resultant solution to 7.2
  Polypeptone: 1%
  Molasses: 1%
  Meat extract: 1%

100 ml of the medium thus prepared was sterilized in a 500-ml Erlenmeyer flask and inoculated with a loopful of spores collected from a slant culture of *Actinomadura roseoviolacea* R20. The inoculated medium was subjected to shake culture for 5 days at 27° C. on a rotary shaker operating at 200 r.p.m. to prepare an inoculum.

(2) Cultivation

A fermentation medium was prepared by dissolving the following ingredients in water and adjusting the pH of the resultant solution to 7.4.
  Glucose: 2.5%
  Soy bean meal: 1.5%
  Dry yeast: 0.2%
  Calcium carbonate (precipitated): 0.4%

25 liters of the fermentation medium was sterilized in a 50-l jar fermenter, and 3 vials of the inoculums prepared as described above were added to the sterilized medium. The fermentation was carried out for 7 days at 27° C. at 1 v.v.m. and 200 r.p.m.

(3) Isolation of R20X

The fermented mash was filtered, and the mycelial cake was separated from the filtrate. The filtrate was adjusted to pH 2 with 1N hydrochloric acid and adsorbed onto "Diaion HP20" (supplied by Mitsubishi Kasei K.K., Japan) packed in a 10×40 cm column. The filtrate thus adsorbed was washed with distilled water and 60% methanol and then eluted with methanol. The eluate was concentrated, adjusted to pH 8.5, and extracted three times with a chloroform-methanol (9:1) mixture. The extract was concentrated, and 6-fold volume of hexane was added thereto. The precipitate formed was dried to obtain 250 mg of a red powder (crude product of R20 substances).

250 mg of this crude R20 substance product was dissolved in chloroform and applied to a 4×40 cm column wherein 250 g of silica gel was equilibrated with chloroform. After the column was thoroughly washed with chloroform, the crude product was fractionated with a 10:1 chloroform-methanol mixture. Fractions thus obtained were concentrated to dryness under reduced pressure and developed on TLC ("Silica Gel 60", Merck & Co., Inc.) by using a 40:8:1:1 chloroform-methanol-acetic acid-water solvent mixture, and thereafter reddish orange fractions having Rf values of approximately 0.43 were scraped off. The fractions thus obtained were eluted, concentrated, and recrystallized from chloroform to yield 110 mg of R20X.

(4) Isolation of R20X2

The fermented mash was filtered, and the mycelial cake was separated from the filtrate. The filtrate was adjusted to pH 2 with 1N hydrochloric acid and adsorbed onto "Diaion HP20" (supplied by Mitsubishi Kasei K.K., Japan) packed in a 10×40 cm column. The filtrate thus adsorbed was washed with distilled water and 50% methanol and then eluted with methanol. The eluate was concentrated, adjusted to pH 8.5, and extracted three times with a chloroform-methanol (9:1) mixture. The extract was concentrated, and 6-fold volume of hexane was added thereto. The precipitate formed was dried to obtain 250 mg of a red powder (crude product of R20X2).

250 mg of this crude R20X2 product was dissolved in chloroform and applied to a 4×40 cm column wherein 250 g of silica gel was equilibrated with chloroform. After the column was thoroughly washed with chloroform, the crude product was eluted with a 10:1 chloroform-methanol mixture. Fractions thus obtained were concentrated to dryness under reduced pressure and developed on TLC ("Silica Gel 60", Merck & Co., Inc.) by using a 8:2:0.05 chloroform-methanol-ammonia water solvent mixture, and thereafter orange fractions having Rf values of approximately 0.44 were scraped off. The fractions thus obtained were eluted, concentrated, and recrystallized from chloroform to yield 10 mg of R20X2.

EXAMPLE 2

Production of 3'-deamino-3'-(4-morpholinyl)-R20X 135 mg (0.27 mM) of R20X was dissolved in 15 ml of chloroform. To the resulting solution were added 320 mg (2.66 mM) of diglycol aldehyde and 17 mg (0.27 mM) of sodium cyanoborohydride dissolved in a 1:1 acetonitrile-water solvent mixture to cause reaction at room temperature for one hour.

Upon completion of the reaction, the reaction solution was extracted three times with 50 ml of chloroform, and the chloroform solution was washed three times with 40 ml of water. The resulting chloroform solution was dried with sodium sulfate anhydride and then concentrated to dryness.

The crude product obtained was applied to silica gel ("Wakogel C-200", 10 g) column chromatography and eluted with a 200:1 chloroform-methanol solvent mixture to obtain the desired product. This product was further crystallized from a chloroform-hexane mixture to yield 90 mg (58%) of the title compound.

EXAMPLE 3

Production of 3'-deamino-3'-(4-morpholinyl)-R20X2

80 mg (0.16 mM) of R20X2 was dissolved in 10 ml of chloroform. To the resulting solution were added 186 mg (1.6 mM) of diglycol aldehyde and 9.8 mg (0.16 mM) of sodium cyanoborohydride dissolved in a 1:1 acetonitrile-water solvent mixture to cause reaction at room temperature for one hour.

Upon completion of the reaction, the reaction solution was extracted three times with 50 ml of chloroform, and the chloroform solution was washed three times with 40 ml of water. The resulting chloroform solution was dried with sodium sulfate anhydride and then concentrated to dryness.

The crude product obtained was applied to silica gel ("Wakogel C-200", 10 g) column chromatography and eluted with a 200:1 chloroform-methanol solvent mixture to obtain the desired product. This product was further crystallized from a chloroform-hexane mixture to yield 42 mg (48%) of the title compound as a brown powder.

EXAMPLE 4

Production of R20Y5

(1) Inoculum Preparation

A medium used to grow a primary inoculum was prepared by dissolving the following ingredients in 1 liter of water and adjusting the pH of the resultant solution to 7.2.

Polypeptone: 1%
Molasses: 1%
Meat extract: 1%

100 ml of the medium thus prepared was sterilized in a 500-ml Erlenmeyer flask and inoculated with a loopful of spores collected from a slant culture of *Actinomadura roseoviolacea* R20. The inoculated medium was subjected to shake culture for 5 days at 27° C. on a rotary shaker operating at 200 r.p.m. to prepare an inoculum.

(2) Cultivation

A fermentation medium was prepared by dissolving the following ingredients in water and adjusting the pH of the resultant solution to 7.4.

Glucose: 2.5%
Soy bean meal: 1.5%
Dry yeast: 0.2%
Calcium carbonate (precipitated): 0.4%

25 liters of the fermentation medium was sterilized in a 50-l jar fermenter, and 3 vials of the inoculums prepared as described above were added to the sterilized medium. The fermentation was carried out for 7 days at 27° C. at 1 v.v.m. and 200 r.p.m.

The fermented mash was filtered, and the mycelial cake was separated from the filtrate. The filtrate was adjusted to pH 2 with 1N hydrochloric acid and adsorbed onto "Diaion HP20" (supplied by Mitsubiishi Kasei K.K., Japan) packed in a 10×40 cm column. The filtrate thus adsorbed was washed with distilled water and 50% methanol and then eluted with methanol. The eluate was concentrated, adjusted to pH 8.5, and extracted three times with a chloroform-methanol (9:1) mixture. The extract was concentrated, and 6-fold volume of hexane was added thereto. The precipitate formed was dried to obtain 250 mg of a powder.

This powder was applied to a 5×40 cm silica gel ("Silica Gel 60", Merck & Co., Inc.) column equilibrated with a 70:10:1 chloroform-methanol-water mixture, and yellow fractions were separated. Fractions thus obtained were concentrated to dryness under reduced pressure and developed on TLC ("Silica Gel 60", Merck & Co., Inc.) by using a 40:8:1:1 chloroform-methanol-acetic acid-water solvent mixture. Subsequently, yellow fractions having Rf values of approximately 0.50 were scraped off. These fractions were eluted, concentrated, and then recrystallized from chloroform to yield 1.6 mg of R20Y5.

EXAMPLE 5

Production of 3'-deamino-3'-(4-morpholinyl)-R20Y5

99.5 mg (0.21 mM) of R20Y5 was dissolved in 5 ml of a 1:1 acetonitrile-water mixture. To the resulting solution were added 246 mg (2.05 mM) of diglycol aldehyde and 12.9 mg (0.21 mM) of sodium cyanoborohydride to cause reaction at room temperature for 4 hours.

Upon completion of the reaction, the reaction solution was diluted with 50 ml of water. The precipitate formed was removed through a glass filter and washed with 50 ml of water. The filtrate was then extracted three times with 50 ml of chloroform, and the chloroform layer was further washed several times with 50 ml of water. The resulting chloroform layer was dehydrated with sodium sulfate anhydride and concentrated to dryness. The material thus obtained is a crude product in combination with the above precipitate. This crude product was applied to slilica gel ("Wakogel C-200") column chromatography and eluted with a 50:1 chloroform-methanol solvent mixture to obtain the desired product. The product thus obtained was crystalized from a chloroform-hexane mixture to yield 42.2 mg of the title compound.

EXAMPLE 6

40 mg of R20X was dissolved in 4 ml of DMF. To the resulting solution were added 260 mg of bis-(2-iodoethyl) ether and 32 mg of triethylamine. The mixture thus obtained was stirred for 4 days at room temperature. The DMF was then distilled off by concentration under vacuum while the residue was dissolved in 100 ml of chloroform, washed with 100 ml of water, dehydrated with sodium sulfate anhydride and then concentrated. The resultant chloroform layer was applied to silica gel chromatography and eluted with a 50:1 chloroform-methanol solvent mixture to obtain two colored fractions. From the fraction eluted first was obtained 5 mg of 3'-deamino-3'-(4-morpholinyl)-R20X while from the fraction eluted later was obtained 7 mg of 3'-deamino-3'-(4-morpholinyl)-R20X2.

What is claimed is:

1. An anthracycline compound of the formula

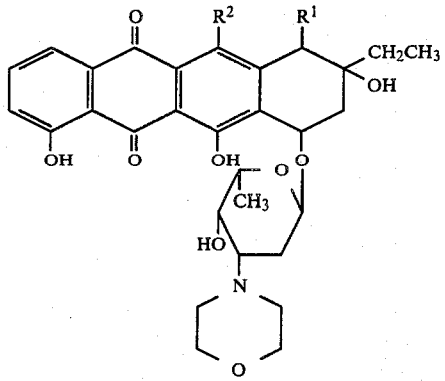

wherein $R^1$ and $R^2$ are at the same time both hydroxyl groups, or both hydrogen atoms or an acid addition salt thereof.

2. A compound, as in claim 1 wherein $R^1$ and $R^2$ are hydrogen atoms or an acid addition salt thereof.

3. A compound, as in claim 1 wherein $R^1$ and $R^2$ are hydroxyl groups or an acid addition salt thereof.

* * * * *